United States Patent [19]
della-Cioppa et al.

[11] Patent Number: 5,814,495
[45] Date of Patent: *Sep. 29, 1998

[54] MELANIN PRODUCTION BY STREPTOMYCES

[75] Inventors: Guy della-Cioppa; Stephen J. Garger, Jr.; Genadie G. Sverlow; Thomas H. Turpen; Laurence K. Grill; Miles R. Chedekal, all of Vacaville, Calif.

[73] Assignee: Biosource Technologies, Inc., Vacaville, Calif.

[ * ] Notice: The term of this patent shall not extend beyond the expiration date of Pat. No. 5,529,909.

[21] Appl. No.: 404,384

[22] Filed: Mar. 14, 1995

Related U.S. Application Data

[60] Continuation of Ser. No. 857,602, Mar. 20, 1992, Pat. No. 5,631,151, which is a division of Ser. No. 607,119, Nov. 2, 1990, abandoned, which is a continuation-in-part of Ser. No. 545,075, Jun. 29, 1990, abandoned, which is a continuation-in-part of Ser. No. 251,809, Oct. 3, 1988, abandoned.

[51] Int. Cl.$^6$ .............................. C12P 17/14; A61K 7/44
[52] U.S. Cl. ........................... 435/120; 424/60; 435/191; 435/252.35; 435/253.5
[58] Field of Search .................. 435/69.2, 69.7, 435/71.2, 128, 170, 193, 244, 252.33, 252.35, 320.1, 886, 888, 191, 120, 253.5; 530/350; 424/78.03, 70.6, 60; 8/405; 536/23.2, 23.4

[56] References Cited

FOREIGN PATENT DOCUMENTS

| 0213898 | 3/1987 | European Pat. Off. . |
|---|---|---|
| WO-A-8802372 | 7/1988 | WIPO . |

OTHER PUBLICATIONS

Bolt, (1967) "Interactions Between Human Melanoprotein and Chlorpromazine Derivatives I. Isolation and Purification of Human Melanoprotein From Hair and Melanoma Tissue," *Life Sci.* 6:1277–1283.

Crameri et al., 1982, "Secretion of Tyrosinase in *Streptomyces glaucescens*," *J. Gen. Micro* 128: 371–379.

Della–Cioppa et al., 1991, "Engineering of novel melanin pigments by expression of tyrosine genes in *Escherichia coli*," *Enzyme and Microbial Technology* 13 (6):522.

Gulyas, F., 1978, "Studies of pigment formation by Actinomycetes," *Chem. Abstracts 89* (15): 294 abstract 125900n & Soil Biol. Conserv. Biosphere (Proc. Meet.) 7th 1975 (Pub. 1977), 265–270.

Hintermann et al., 1985, "Cloning and expression of the genetically unstable tyrosinase structural gene from *Streptomyces glaucescens*," *Mol. Gen. Genet. 200*:422–432.

Morino et al., 1988, "Interspecific transfer and expression of melanin gene(s) on cosmids in *Streptomyces* strains," *Applied Microbiology and Biotechnology* 27 (5/6):517–520.

Pavlenko et al., 1981 "Melanin pigment of Gluconobacter oxydans," *Chem. Abstracts 95(19)* : 379, abstract 165240c.

Pirt et al., 1970, "Melanin production in *Aspergillus nidulans*," *Chem. Abstracts 72(1)* :78, abstract 878d & Biochem. J. 1969, 114(1), 9P–10P.

Pizlo et al., 1983, "Crude melanins from postrectification spirits," *Chemical Abstracts,* 98(1):325, abstract 3561t & PL–A–144875 (Akademia Rolnicza).

Planten et al., 1987, "Effect of copper on growth and tyrosinase activity of streptomycetes,"*Chemical Abstracts,* 108(15):417, abstract 128189j & VDLUFA–Shriftenr (Leistungsfoerderer Tierprod.)

Rowley et al., 1978, "Influence of growth rate history on production of melanin by *Aspergillus nidulans*," *Trans. Br. Mycol. Soc. 73(3)* :453–455.

*Primary Examiner*—Keith D. Hendricks
*Attorney, Agent, or Firm*—Albert P. Halluin; Howrey & Simon

[57] ABSTRACT

The present invention is directed to a process for producing melanins, their precursors and their analoges, hereinafter referred to generically as melanins. According to the invention, melanins are produced in amounts greater than about 3.3 grams wet weight per liter of growth medium. The enhanced production of melanin can be achieved by manipulating the constituents of the growth medium, and/or attenuating fermentations conditions, and/or by genetically engineering microorganisms to produce melanins, and/or mutating the microorganisms.

12 Claims, 29 Drawing Sheets

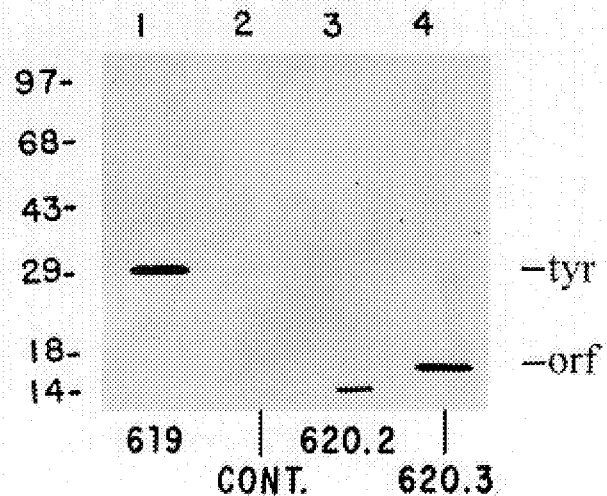
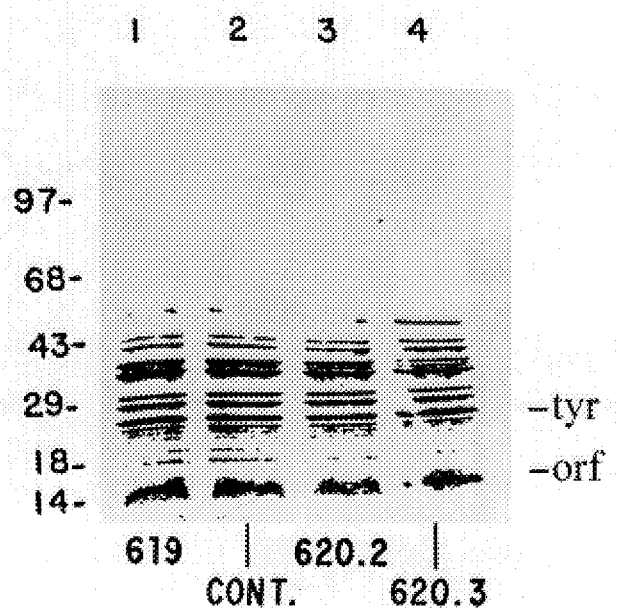

(FIG. 4C)

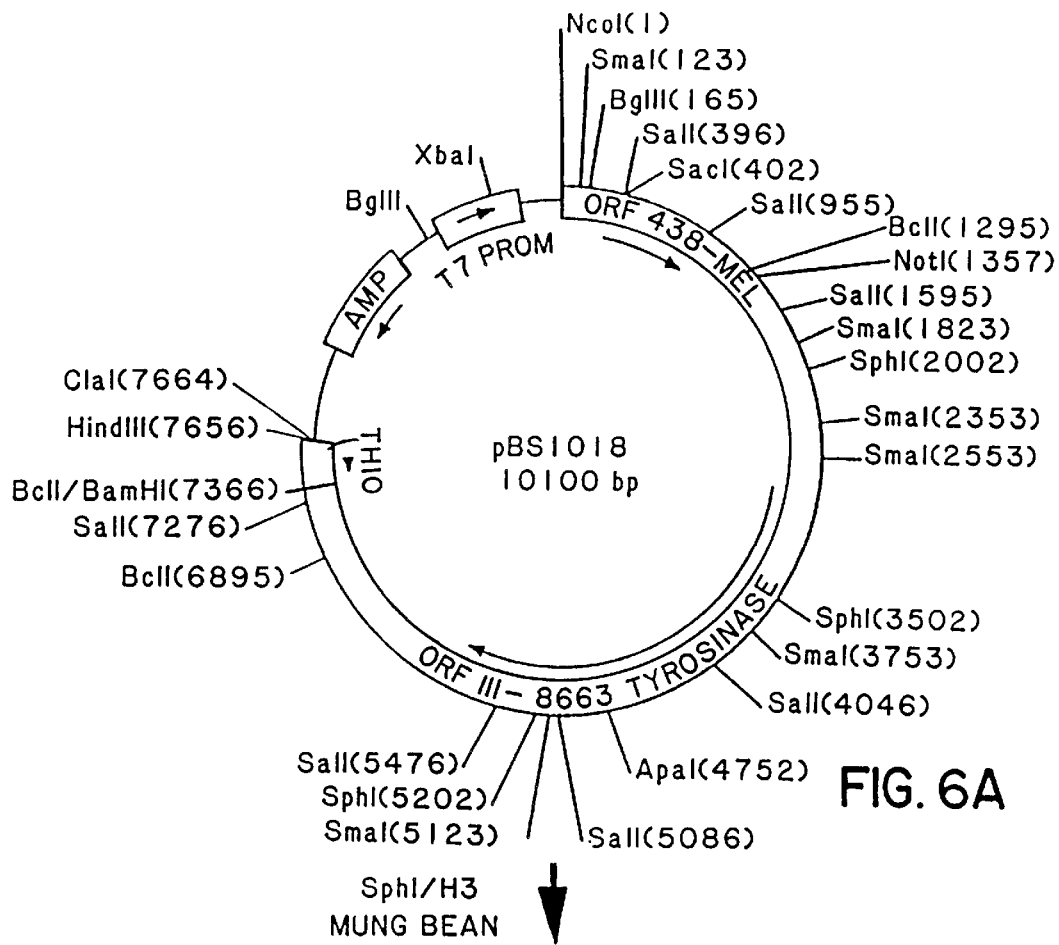
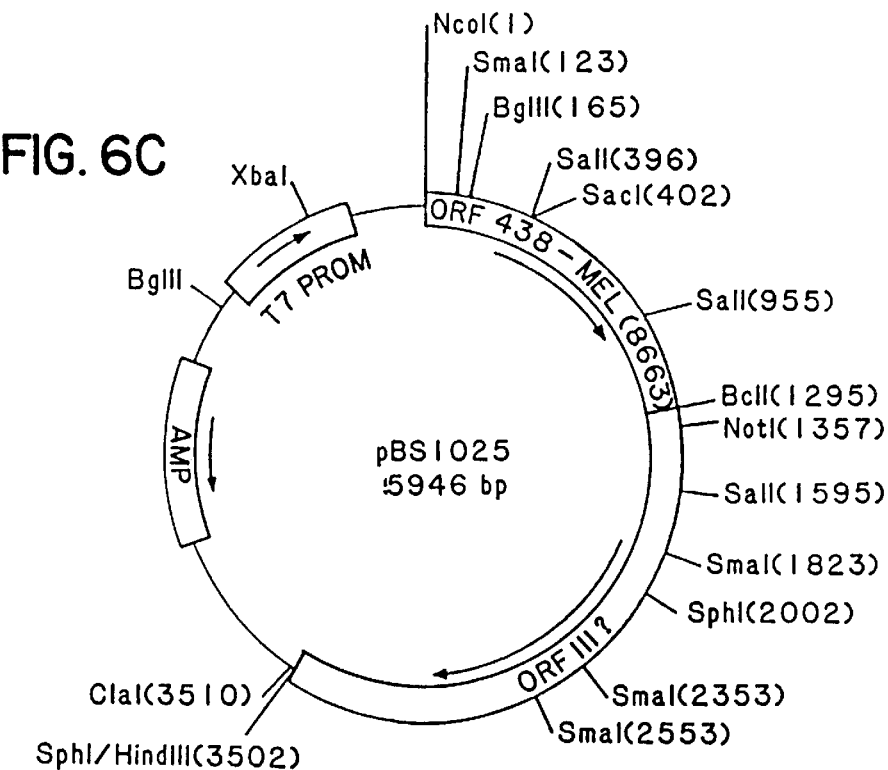
FIG. 6A
FIG. 6C

MELANIN PRODUCTION BY STREPTOMYCES

This application is a continuation application of Ser. No. 857,602, filed Mar. 20, 1992, now U.S. Pat. No. 5,631,151 which is a divisional application of Ser. No. 607,119, filed Nov. 2, 1990, abandoned, which is a continuation-in-part of Ser. No. 545,075, filed Jun. 29, 1990, abandoned, which is a continuation-in-part of U.S. application Ser. No. 251,809 filed Oct. 3, 1988, abandoned, incorporated herein by reference.

BACKGROUND OF INVENTION

Melanin the Biopolymer

Melanogenesis, production of the biological polymer melanin, is a widespread phenomena in nature occurring in most phyla from fungi to mammals. Tyrosinase (E.C. 1.14.18.1), is known to catalyze melanin formation and is present in bacteria, fungi, gymnosperms, angiosperms, arthropods and chordates. The black, brown, buff and Tyndall-blue pigments found in feathers, hairs, eyes, insect cuticle, fruit and seeds are usually melanins and are assumed to result from the action of tyrosinase. The enzyme is not universal; it occurs relatively rarely in prokaryotes, is absent in a variety of higher plants and is generally confined to specific cells of the skin in higher animals but may occur in interior tissue, such as the substantia nigra, eye and inner ear. Melanins have been assigned a photoprotective role in the skin, their role in the eye and inner ear in unknown.

The mammalian melanins are subdivided into two chemical classes; eumelanins (the brown to black pigments derived from 3,4-dihydroxyphenylalanine [dopa] oxidation products) and pheomelanins (the red to yellow pigments derived from cysteinyldopa oxidation products). The intractable nature of these pigments has made their characterization and quantification experimentally difficult. In humans, eumelanins and pheomelanins exist as an intimate mixture, the ratio of eumelanin to pheomelanin being genetically determined.

The stepwise biosynthesis of melanins is presented in FIG. 1. The first two steps of eu- and pheomelanogenesis are catalyzed by the tyrosine hydroxylase (TH) and dopa oxidase (DO) activities of tyrosinase. Both eu- and pheomelanogenesis proceed by the same pathway to dopaquinone. In the absence of sulfhydryl compounds, eumelanin results. Dopaquinone and its subsequent cyclized intermediates may form eumelanin through a series of nonenzymatic steps. The reactions distal to dopaquinone proceed spontaneously at room temperature and were originally thought to be unregulated. The rate constants, k, for some of these post-dopaquinone reactions en route to eumelanin have been reported.

| | | Rate constant, k |
|---|---|---|
| dopaquinone | cyclodopa | $134\ s^{-1}$ (pH 5.4) |
| dopaquinone + cyclodopa | dopachrome + dopa | $10^9\ s^{-1}\ M^{-1}$ (pH 7.7) |
| dopachrome | 5,6-dihydroxy indole | $5.8 \times 10^{-5}\ s^{-1}$ (pH 5.1) |

Chemical regulation of melanogenesis is assumed to be the result of general acid-base catalysis or electrostatic catalysis by nucleophiles and electrophiles inherent to the reaction medium. More notably, the changes in the ionic strength of the reaction medium regulate catalysis by influencing the polarizability of the melanogenic precursors and intermediates. The reaction medium itself may cause solvent-solute interactions which influence permanent or induced dipoles. Regulation is also manifested when changes in pH change the degree of ionization of reactants or the medium. Finally, molecular interactions such as hydrogen bonding, dimerization or ion pair formation among the reactants or medium may regulate melanogenesis.

The following list of "melanin facts" must be kept in mind when trying to define, characterize, or quantify melanin polymers:

1. Melanogenesis not only affords melanins, but also a number of "melanochromes" such as 5,6-dihydroxyindoles, cysteinyldopas and trichochromes.
2. Melanins are more properly referred to as melanoprotein, and are composed of a protein fraction intimately bound to a chromophore.
3. Melanins are known to exist in nature as particles, and it has been demonstrated that the isolation protocol can irreversibly change the nature of the melanin granule.
4. Alkaline peroxide treatment of melanin yields "solubilized" melanin termed melanin free acid (MFA).
5. When heated above 100° C. melanin readily gives off carbon dioxide (this process has been assigned to decarboxylation of aryl carboxylic acid residues present in the polymer).
6. Melanin exhibits ion exchange properties which have been postulated to have importance for the biological function of the pigment.

The literature is replete with reports concerning the physical, chemical and biological properties of melanins which have been isolated from animal and plant systems. However, the isolation techniques reported have been poorly designed. They are often chemically harsh and rarely take into consideration the inherent reactivity of melanins. The following three examples depict protocols which are commonly referenced in the literature:

A. " . . . melansosomes were collected from HP melanoma and secondly the melanin was washed extensively with tetrahydrofuran (THF) to extract impurities. In this step, THF was coloured to yellow. The sample was then dried and was dissolved in alkaline solution, e.g., ethylene diamine water solution (30/100 volume ratio) and/or 1N $NH_4OH$ water solution. A large volume of 12N HCl water solution was poured into this melanin solution which was then boiled for 30 hours and remained to rest. The precipitated melanin was collected, washed repeatedly, and dialyzed and dried. Finally melanin was washed by THF repeatedly until THF became colourless and then dried." From "Chemico-Physical properties of Melanin (II)."

B. " . . . The black precipitate, collected by centrifugation, was kept in conc HCl at room temp for 7 days. After centrifugation, the melanin was thoroughly washed with 1% HCl, distilled water and finally acetone." From "The Structure of Melanins and Melanogenesis-II."

C. "The eyes were dissected to separate the iris, ciliary body, choroid and retinal pigment epithelium. These fractions were pooled and suspended in distilled water and then homogenized. The homogenate was filtered through four layers of gauze and the filtrate was mixed with an equal volume of concentrated HCl to give a final concentration of 6N HCl.

The mixture was stirred for 24 hours; the precipitate was removed by centrifugation, resuspended in 6N HCl, and refluxed for 48 hours. The precipitate was washed with water 4–6 times and suspended in water." From "Do the Melanins from Blue and Brown Human Eyes Differ?" Menon, I. A., et al. Pigment Cell 1981, *Proceedings of the XI International Pigment Cell Conference Sendai*, Japan, pp. 17–22 (1981).

The hypothetical structure of melanin depicted below, incorporates the work of numerous groups over the last five decades. For reviews, see Swan, G. A. *Fortschritte of Chem. Org. Naturst.* XXXI, 552; (1974); Proto, G. *Medical Research Reviews* 8, 525 (1988); and Ito, S. *Biochim. Biophys. Acta* 883, 155 (1986).

The study of melanins has led to the discovery of a number of pathways of biosynthesis and also to a wide variety of chemicals related to melanins. Fungal melanins occur as wall-bound melanins and extracellular melanins. Most hyphal, conidial, and sclerotial walls of melanized fungi appear to have two distinct layers: an inner layer which is electron translucent and an outer layer containing electron-dense granules. Collective evidence shows that these granules are melanins, Wheeler, M. H. et al., *Exp. Mycol.* 3, 340 (1979). Extracellular melanins are synthesized apart from cell walls. They are derived from phenols by two mechanisms: (a) oxidation of phenolic compounds by phenol oxidases (sometimes also called phenyloxidase) secreted into the medium and (b) oxidation of phenols secreted into the medium either by autooxidation or by enzymes released during autolysis. Wheeler, M. H. et al., Can *J. Microbiol.* 24, 289 (1978).

Fungi or bacteria which secrete tyrosinase cause discoloration of the surrounding medium. That discoloration can be accentuated by adding tyrosine to the medium, Hollis, J. P., *Phytopathology* 42, 273 (1952); Nurudeen, T. A. et al., *J. Clin. Microbiol.* 10, 724 (1979). Extracellular melanins have been observed in Actinomycetes, bacteria, and fungi. Genes controlling extracellular tyrosinase production or secretion occur on plasmids in *Streptomyces scabies*, Gregory, K. F. et al., *J. Bacteriol.* 87, 1287 (1964), and *Rhizobium phaseoli* strain 1233, Beynon, J. L. et al., *J. Gen. Microbiol.* 120, 421 (1980). The tyrosinase gene in *Vibrio cholerae* is located on the chromosome. Bell, A. A. et al., *Ann. Rev. Phytopathol.* 24, 411 (1986).

In one of the melanin pathways, synthesis of Eumelanin is mediated by tyrosinase which is generally agreed to catalyze the first two steps in the biosynthesis. The initial reaction involves the hydroxylation of tyrosine. An oxygen atom is incorporated adjacent to the hydroxyl group of tyrosine to produce 3,4-dihydroxyphenylalanine (DOPA). Tyrosinase then catalyses the conversion of DOPA to dopaquinone. The dopaquinone formed is not stable at physiological pH. The amino group of the side chain cyclizes to give cyclodopa which then oxidizes rapidly to dopachrome, a red compound. The next step is a rearrangement and decarboxylation to give 5,6-dihydroxyindole (DHI) or without decarboxylation to produce 5,6-dihydroxyindole-2-carboxylic acid (DHICA). The eumelanins are formed from the polymerization of dopaquinone, dopachrome, DHI and DHICA or combinations thereof. These form the brown pigments in animals. Mason, H. S., *J. Biol. Chem.* 172, 83 (1948); and Pawelek, J. M. et al., *Am. Sci.* 70, 136 (1982). Crippa et al., *The Alkaloids* 36, 253 (1989), Academic Press N.Y., N.Y.

Phaeomelanins, the red, brown and yellow pigments of animals are polymers of cysteinylDOPAs which are derived from mixed cystein and tyrosine. Fitzpatrick, T. B. et al., in *Biology and Diseases of Dermal Pigmentation* p. 3, Univ. Tokyo Press, Tokyo. Trichochromes are also classified with melanins since they are yellow, red and violet pigments and they are derived from the oxidation of tyrosine.

Allomelanins which contain little or no nitrogen are formed from phenolic precursors, primarily catechol and 1,8 dihydroxynaphthalene.

Tyrosinase is not the only melanin producing enzyme. Laccase, an enzyme found in the outer walls of fungi is responsible for the oxidation of DOPA. Laccase will not readily oxidize tyrosine. Simon, L. T. et al., *J. Bacteriol.* 137, 537 (1979). Other enzymes present in pigment producing organisms are phenyloxidase of *Cryptococcus neoformans* as well as catechol oxidase and other polyphenol oxidases of plants. Mayer, A. M. et al., *Phytochem.* 18, 193 (1979).

γ-glutaminyl-3,4-hydroxybenzene (GDHB) melanin is synthesized from γ-glutaminyl-4-hydroxybenzene (GHB) by that action of tyrosinase in *Agaricus bisporus*. Hegnauer, H. et al., *Exp. Mycol.* 9, 221. *Ustilago maydis* is believed to metabolize catechol to melanins. Teleospores of *U. maydis* produce highly election dense melanins when fixed with $OsO_4$. Patgieter, H. J. et al., *J. Bacteriol.* 91, 1526 (1966).

Biosynthesis of 1,8-dihydroxynaphthalene (DHN) melanin is produced from pentaketide. A variety of intermediates occur including 1,3,6,8-tetrahydroxynaphathlene, scytalone, 1,3,8-trihydroxylnaphthalene, vermelone, dihydroxynaphthalene, dihydroxynaphthalene 1,1-dimer and dihydroxynaphthalene 2,2-dimer. Mutational blocks eliminating reductase or dehydratase enzymes, and enzyme inhibitors such as tricyclazole cause the occurrence of a large number of shunt products. Wheeler, M. H. et al., *Arch. Microbiol.* 142, 234 (1985); and Stipanovic, R. D. et al., *Pestic. Biochem. Physiol.* 13, 198 (1980).

Culture conditions vary among different microorganisms. Production of extracellular melanins in some microorganisms has been shown to increase as the concentration of tyrosine is increased to its saturation point of 0.1 percent. This percentage is considered supersaturation in tyrosine. Hollis, J. P. (1952), supra. It has been reported that yeast autolysates and casein hydrolysate stimulate melanin pigment production by *Streptomyces scabies* in a medium containing 0.1% percent tyrosine. Hollis, J. P. (1952), supra.

It has also been shown that production of melanins is repressed by a variety of carbon sources. The particular carbon source varies with the microorganism. Nurudeen, T. A. et al. (1979), supra, reported that increased glucose concentration in the medium reduced pigmentation of all serotypes of *Cryptococcus neoformans*. This fungus produces melanin-like pigments with diphenol and aminophenol through the mediation of a phenyloxidase enzyme. The phenyloxidase of *C. neoformans* cannot use tyrosine as a substrate. In contrast to the metabolism of Cryptococcus, *Gluconobacter oxydans*, a pigment producing bacterium produces melanin in the presence of glucose and tyrosine, but not in a medium containing sucrose, fructose, sorbitol, mannitol or glycerol as the carbon source. Pavlenko, G. V. et al., *Microbiology USSR* 50, 539 (1981).

Several fungi are known to produce extracellular heterogenous melanins. These melanins are derived from various phenols, amino acids, proteins, carbohydrates and lipids. Synthesis requires secretion of tyrosinase into the medium.

Many species of Streptomyces are capable of forming dark melanin pigments due to expression of tyrosinase from the mel gene locus. The mel locus of *S. antibioticus* has been cloned and sequenced, Katz, E. et al., *J. Gen. Microbiol.* 123, 2703 (1983); Bernan, V. et al., *Gene* 37, 101 (1985) and shown to contain two open reading frames (ORF's) that encode a putative ORF438 protein ($M_r$=14,754) and tyrosinase ($M_r$=30,612). ORF438 and tyrosinase are thought to be transcribed from the same promoter in *S. antibioticus*, and both genes are required for melanin production. Bernan, V. et al., (1985), Supra. Based on genetic evidence, ORF438 protein has been shown to function as a trans-activator of tyrosinase. Lee, Y.-H. W. et al., *Gene* 65, 71 (1988). It has been suggested that the ORF438 protein is involved in tyrosinase secretion, or it may function as a metallothionein-like protein that delivers copper to apotyrosinase, Bernan, V. et al., (1985), Supra; Lee, Y.-H. W. et al., (1988), Supra. The mel locus of *S. glaucescens* has a nearly identical ORF sequence upstream of tyrosinase that probably serves a similar function. Huber, M. et al., *Biochemistry* 24 6038 (1985); Huber, M. et al., *Nucleic Acids Res.* 15 8106 (1987). The existence of an ORF438 protein, however, has never been confirmed in vivo.

Naturally occurring *E. coli* does not have a tyrosinase gene and does not produce melanin. The BclI fragment of plasmid pIJ703 encoding the tyrosinase gene of *Streptomyces lividans* was cloned into plasmid YEp13 at the BamHI site and transformed into *E. coli* HB101. There was no detectible expression of tyrosinase or expression of melanin. Nayak, K. et al., *Indian Journal of Biochemistry & Biophysics* 25, 515 (1988).

U.S. Pat. No. 4,898,814 issued to Kwon discloses a cDNA clone of human tyrosinase and claims a method of making human tyrosinase by expressing the cDNA in *E. coli*.

Melanin production in *Shewanella colwelliana*, a gram negative marine bacterium, has been analyzed by measuring L-DOPA synthesis in crude extracts. The region encoding-melanin syntheses was mapped and sequenced. A pair of open reading frames (ORF) were found. One ORF was found to correspond to the tyrosinase gene. The downstream ORF encoded a polypeptide of unknown function. Deletion of the downstream ORF was found to have no effect on pigmentation in *E. coli* transformed with the tyrosinase gene. Fuqua, W. et al., *Abstract, American Society for Microbiology* Washington, D.C. Branch of George Mason University (1990).

SUMMARY OF INVENTION

The present invention is directed to a process for producing melanins, their precursors and their analogues, hereinafter referred to generically as melanins. According to the invention, melanins are produced in amounts greater than about 0.2 grams dry weight per liter of growth medium. The enhanced production of melanin can be achieved by manipulating the constituents of the growth medium, and/or attenuating fermentations conditions and/or by genetically engineering microorganisms and/or by mutagenesis to produce melanins. Melanin producing microorganisms will generally proliferate in a variety of media known in the art for the microorganism from which it was derived. However a growth medium may be enhanced by the addition of special factors in order to increase the yield of melanins or to direct the yield of melanin precursors or derivatives and/or by the deletion of factors which negatively affect the yield of melanins. In addition, the composition of the melanins produced by the microorganism can be controlled by the precursors introduced into the growth medium.

Suitable microorganisms are produced by mutagenesis and/or transformation by a number of methods conventional in the art. Mutagenesis is carried out by a number of methods which include, for example, radiation and exposure to mutagenic chemicals. Vectors which contain genes coding for enzymes which catalyze conversion of melanin precursors and an appropriate promoter for expression in the desired host are used to transform microorganisms which either do not produce melanins or which produce melanins in commercially unsatisfactory amounts.

BRIEF DESCRIPTION OF THE FIGURES

FIG. 3. SDS-PAGE of *E. coli* cells producing tyrosinase with and without ORF438 protein. (A) [$^{35}$S] Methionine autoradiograph of protein synthesized in vivo in the presence of rifampicin (lane 1, pBGC619; lane 2, pT7-7 vector control; lane 3, pBGC620.2; lane 4, pBGC620.3). The film shown is a 2 hr exposure. (B) Coomassie stained gel (lane 1, pT7-7 vector control; lane 2, pBGC619; lane 3, pBGC620.2; lane 4, pGBC620.3). The positions of the molecular weight markers (kD) are shown to the left, and tyrosinase (tyr) and ORF438 (orf) to the right.

DETAILED DESCRIPTION OF THE INVENTION

Figure 1:
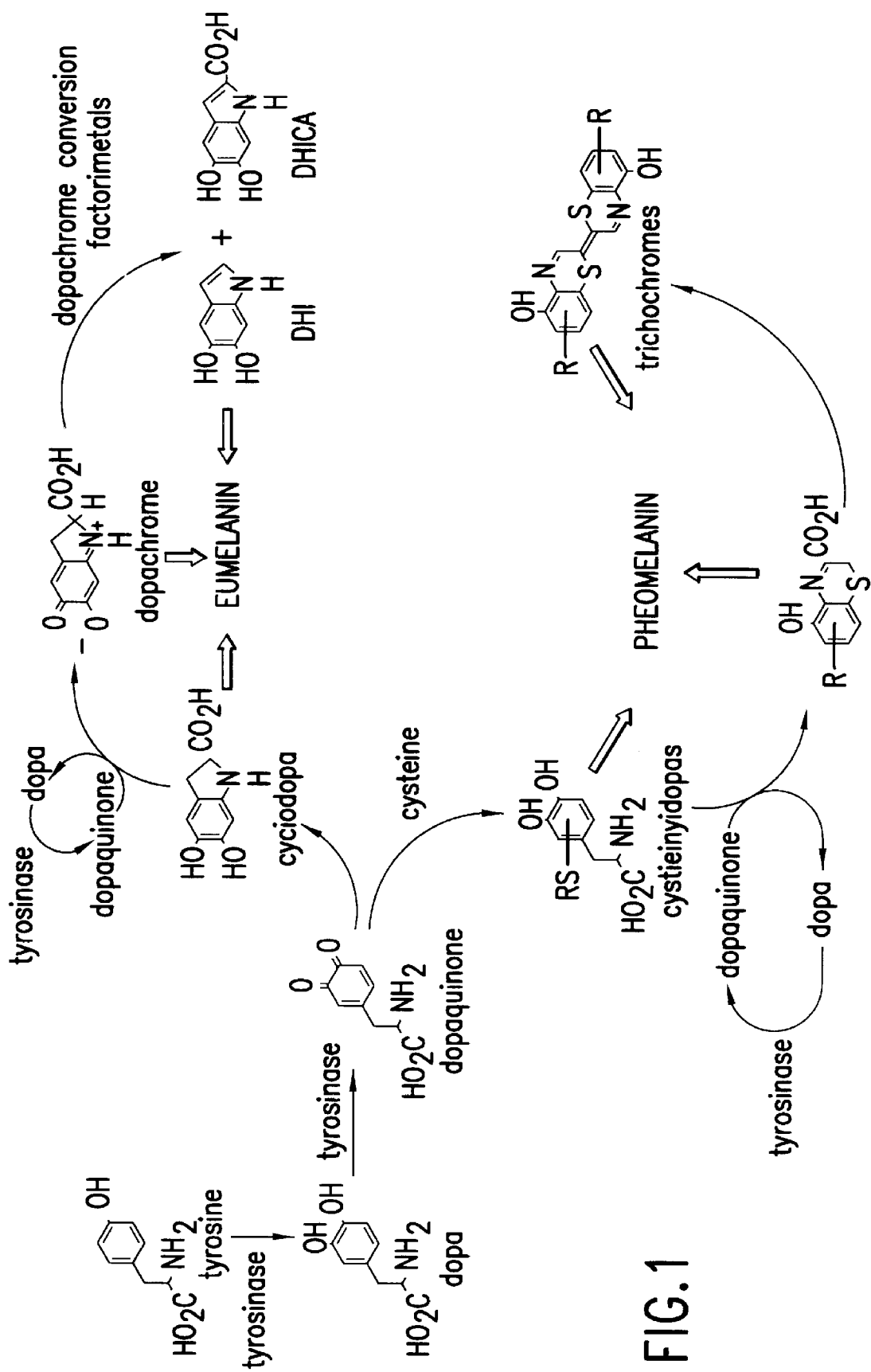
FIG. 1. An illustration of the stepwise bio-synthesis of melanins.

The present invention is directed to melanins and a process for producing melanins, their precursors and their derivatives, hereinafter referred to generically as melanins. According to the invention, melanins are produced in amounts greater than about 0.2 grams dry weight per liter of growth medium. The enhanced production of melanin can be achieved by manipulating the constituents of the growth medium, and/or attenuating fermentation conditions and/or by genetically engineering microorganisms and/or by mutagenesis to produce melanins. The present invention includes: (a) genes, promoters, signal sequences and regulatory sequences capable of transforming microorganisms to produce microorganisms with the capability or enhanced capability of producing tyrosinase and/or melanins; (b) microorganisms with the capability or enhanced capability of producing melanins; (c) a process of producing melanins with a microorganism; (d) a method of isolating melanins from cultures of microorganisms; (e) a growth medium and culture conditions in which melanins can be produced in quantities greater than about 0.2 grams dry weight of melanins per liter of growth medium.

In order to provide a clear and consistent understanding of the specification and the claims, including the scope given to such terms, the following definitions are provided:

Melanin: Melanins are polymers produced by polymerization of reactive intermediates. The polymerization mechanisms include but are not limited to autoxidation, enzyme catalyzed oxidation and free radical initiated polymerization. The reactive intermediates are produced chemically or enzymatically from precursors. Suitable enzymes include, but are not limited to peroxidases and catalases, polyphenol oxidases, tyrosinases, tyrosine hydroxylases or laccases. The precursors which are converted to the reactive intermediates are hydroxylated aromatic compounds. Suitable hydroxylated aromatic compounds include, but are not limited to 1) phenols, polyphenols, aminophenols and thiophenols of aromatic or polycyclic aromatic hydrocarbons, including but not limited to phenol, tyrosine, pyrogallol, 3-aminotyrosine, thiophenol and α-naphthol; 2) phenols, polyphenols, aminophenols, and thiophenols of aromatic heterocyclic or heteropolycyclic hydrocarbons such as but not limited to 2-hydroxypyrrole, 4-hydroxy-1,2-pyrazole, 4-hydroxypyridine, 8-hydroxyquinoline, and 4,5-dihydroxybenzothiazole.

Activator protein: a gene product that alters, activates or enhances the activity of an enzyme and/or melanogenesis. It may function as a trans-activator, as a metallothionein-like protein that delivers an ion to the apoenzyme or it may function in secretion of the enzyme from the cell. For example, the ORF438 gene and ORF(s) 3' to the tyrosinase coding sequence code for activator proteins that enhance melanogenesis in all of the ways described.

Microorganisms that produce melanins are widely distributed in nature. Examples include but are not limited to Streptomyces, Rhizobium, Agaricus, Ustilago, Cryptococcus, Gluconobacter, Pseudomonas, Xanthomonas, Cochliobolus, Pleospora, Alternaria, Aurobasidium, Botrytis, Cladosporium, Diplodia, Sclerotium, Verticillium, Eurotium, Aspergillus, Stachybotrys, Hendersonula, Streptoverticillium, and Micromonospora.

Several microorganisms may be genetically engineered to enable them to produce melanins. They include but are not limited to Streptomyces, Escherichia, Bacillus, Streptococcus, Salmonella, Staphylococcus, and Vibrio.

Industrial pigment production in microorganisms is now possible because extracellular melanins and their derivatives and precursors are easily removed from the medium where they have been synthesized.

Microorganisms that produce melanins or melanin analogs can be enhanced by alteration. Common alterations include plasmid insertion and mutation. Mutation is accomplished by a variety of means conventional in the art. Microorganisms can be exposed to ultraviolet or gamma radiation or mutagenic chemicals.

As previously described, the present invention is directed to the enhanced production of melanin in amounts greater than about 0.2 grams, especially in amounts greater than about 0.5 grams, preferably in amounts greater than about 1.0 grams and most preferably in amounts greater than about 2.0 grams by weight per liter of medium. The enhancement can be achieved by the growth conditions of the microorganisms, such as medium constituents or attenuating fermentation and/or by genetic manipulations and/or mutation.

A. Growth Conditions

The basic composition of the medium used depends upon a number of considerations. The medium is usually chosen from those known in the art for growing microorganisms similar to the one being grown for melanin production. A variety of carbon and nitrogen sources are available and interchangeable. To enhance growth, the specific needs of the microorganism are considered and met. For instance, a microorganism may require a specific amino acid to be present. All microorganisms require metal ions such as iron and manganese but differ in their concentration requirements. Microorganisms are inhibited by the presence of certain metabolites. Inhibition differs widely from one microorganism to the next.

In addition to the metabolic needs of the microorganism the substrates available for enhancing melanin production should be considered. The presence of precursors may enhance the production or alter the composition of the melanin produced and thereby alter its color and its molecular weight or it may result in production of other desirable products. Tyrosinase requires copper. Therefore trace metals must be present in sufficient concentration to act as cofactors for the enzyme without poisoning the medium.

The temperature of the fermentation medium is critical to optimum growth of the microorganism. Typical soil microorganisms grow well at about 26° C. to about 30° C. while *E. coli* grows best at 37° C. and thermophilic microorganisms grow well at around 50° C. and higher.

The pH of the medium is usually maintained between 6.8 and 7.2. A buffering agent which also provides a requirement of the microorganism is often chosen. A phosphate buffer is often used to help maintain the pH of the medium.

Oxidative microorganisms require aeration. In smaller vessels, stirring or shaking is sufficient. In larger fermentation vessels oxygen is sparged into the system and an impeller stirs the medium at a rate sufficient to provide an optimum dissolved oxygen level. This might be around 20–90% for some microorganisms.

One means of enhancing production of melanins is by modification of the growth medium. Applicants have found that several factors can be altered which tremendously increase production of melanins. One factor is to attenuate the fermentation conditions. This is accomplished by maintaining a high level of oxygen availability to the cultured microorganisms. If low levels of oxygen are available or a low degree of aeration is provided, then yields of melanin are reduced. A second factor is the presence of suitable substrates, e.g., casein hydrolysate or casein peptone which contain tyrosine. It has been found that either of these substrates is better than casamino acids for melanin production, A third factor is the presence of precursors. It has been found that the best yields occur at a tyrosine concentration of 1.6 g/l. A fourth factor is to delete from the medium carbohydrates or other substances which act as repressors.

A second means of controlling or enhancing production of melanins is to include activators and/or other regulatory DNA sequences, such as 3' regulatory sequences of tyrosinase genes. As described further below the mel locus from pIJ702 includes an activator coding sequence and a tyrosinase coding sequence. 3' regulatory sequences have also been useful in regulating melanin production in *E. coli* containing the mel region from an *S. antibioticus* strain.

In general, cultures of microorganisms are grown in the selected medium described above to produce the desired level of melanin. The melanin production is observed by measuring the optical density (OD) of cell free media at 400 nm ($OD_{400}$) at various intervals of time. The $OD_{400}$ is directly proportional to the yield of melanin. The $OD_{400}$ is monitored and the cultures are harvested when the OD has leveled off. In *E. coli* cultures producing melanin the OD was read at 600 nm.

By modifying the medium in which *S. lividans* TK64 (pIJ702) is grown, a tremendous increase in melanin production can be achieved. By inventing a medium that lacks a metabolic repressor of the melanin pathway, it has been found advantageously that melanin production can be increased in a fixed volume bioreactor from about 100 mg per liter to about 4.0 grams per liter or more. Production levels of melanin using genetically modified *E. coli* are equivalent.

The present invention includes a growth medium having a nitrogen source rich in one or more melanin precursors. It is also lacking in glucose. It has been found that higher melanin production is achieved with casein peptone than with casein hydrolysate or casamino acids. It has also been found that tyrosinase production is enhanced in *Streptomyces lividans* by the removal of glucose from the medium. There are at least two possible explanations for this effect, although applicants are not bound by these explanations. Glucose might be a preferred carbon and energy source for *S. lividans*. A possible explanation is that glucose is a metabolic inhibitor of tyrosinase or some other enzyme in the biochemical pathway for production of melanins.

For producing melanins using Streptomyces strains, an inoculum of about $10^3$ to about $10^7$, preferably about $10^4$ to about $10^6$, spores per ml produce high melanin yields. In addition, starter culture that is in mid-log phase, about 24–48 hours old may be added to the fermentation vessel at up to 10% volume. For melanin production on agar indicator plates (indicator plates were supplemented with $CuSO4.5H_2O$ (0.2 mM) and L-tyrosine (0.3 g/l)), colonies were grown overnight at 30° C., then 1 hr at 42° C., and followed by additional growth (3 hr to overnight) at 30° C. to allow for visible pigment formation. For melanin production in liquid culture, overnight cultures (30° C.) were diluted 1:50 into fresh LB and grown for 5 hr at 30° C., transferred to a 42° C. shaking water bath for 30 min, and then returned to 30° C. for continued overnight growth. Melanin production in liquid culture also required the addition of $CuSO4.5H_2O$ and L-tyrosine.

In addition to producing melanins, including melanin analogues, the culturing of the microorganisms produces tyrosinase and protein products of related ORFs. Depending on the microorganism cultured, the tyrosinase may be found within the cell or the periplasmic space or excreted into the medium. The production of tyrosinase enables the recovery of either the tyrosinase and associated ORF products themselves or the microorganisms, especially *E. coli*, containing the tyrosinase and associated ORF products for use in a bioreactor such as an enzyme bioreactor or a cell bioreactor. It may then be possible to produce reactive intermediates from melanin precursors which may find other utilities.

The composition of the melanins can be altered by adding different precursors to the growth medium such that melanin and melanin analogues are produced. Melanin analogus are produced when exogenous precursors are added to the media. Investigators have found suitable precursors include but are not limited to:

| | |
|---|---|
| 1-cysteine ethyl ester | 3-nitro-L-tyrosine |
| 3-fluro-DL-tyrosine | 3-methoxy-L-tyrosine |
| L-proline | (±)-synephrine |
| DL-m-Tyrosine | 3-iodo-L-tyrosine |
| 3,4-dihydroxycinnamic acid | glycyl-L-tyrosine |
| L-3,4-DOPA methyl ester | DL-octopamine |
| 4-hydroxyindole | tyramine |
| L-cysteine | L-methionine |
| 5,6-dimethoxyindole | (−)-arterenol |
| D-DOPA | 5-hydroxytryptamine |
| L-tyrosine ethyl ester | protamine sulfate |
| L-tyrosine | L-DOPA |
| | and combinations of precursors. |

Through the use of these precursors, it is possible to alter the chemical properties of the melanins as well as the colors of the melanin which include but are not limited to red, blue, green, black, brown, orange, violet and yellow. In addition, different colors of melanin can be produced by, for example, adding metal ions to the culture medium.

B. Genetic Manipulations

The chimeric genes and vectors of the present invention are constructed and used to transform microorganisms using techniques well known in the art in view of the following description. Suitable techniques have been described in Maniatis, T. et al., *Molecular Cloning*, 1st Ed., Cold Spring Harbor Laboratory, New York (1982); *Molecular Cloning*, 2nd Ed., Cold Spring Harbor Laboratory, New York (1989); *Methods in Enzymology*, Vols. 68 (1979), 100 (1983), 101 (1983), 118 (1986) and Vols. 152–154 (1987); *DNA Cloning*, Glover, D. M., Ed., IRL Press, Oxford (1985); and *Plant Molecular Biology: Manual*, Gelvin, S. B. et al., Eds., Kluwer Academic Publishers, Dodrecht (1988). Medium compositions have been described in Miller, J. H., *Experiments in Molecular Genetics*, Cold Spring Harbor Laboratory, New York (1972), as well as the references previously identified. Hopewood, D. A. et al., "Genetic Manipulation of Streptomyces: A Laboratory Manual", The John Innes Foundation, Norwich, England (1985).

Preparation of DNA Sequences

A DNA fragment from any source can be isolated and prepared by any of a variety of methods that are conventional in the art. For example, the DNA sequence can be isolated from a gene bank of genomic clones or directly from isolated chromosomal DNA. Restriction endonucleases are useful because they allow DNA to be digested, analyzed and restructured in a controlled, site-specific and predictable manner. A DNA sequence obtained from digestion by, for example, EcoRI will fit into an opening at a EcoRI recognition site in the plasmid DNA. The complementary ("sticky") ends are attachable by a T4 DNA ligase.

Digested DNA can be resolved on the basis of molecular weight by polyacrylamide or agarose gel electrophoresis. DNA fragments separated on an electrophoresis gel can be identified by a number of methods known in the art. They may be bound to protein or RNA and identified by electrophoresis. They may be probed by RNA or DNA after being lifted from a gel to cellulose nitrate filter paper. The RNA or DNA probe either carries a radioactive species or a detectable enzyme. Smith, G. et al., *Anal. Biochem.* 109, 123 (1980); and Southern, E. M. *J. Mol. Biol.* 98, 503 (1975). Synthetic oligonucleotide DNA probes are usually about 12 or more bases in length. If the sequence of the DNA or RNA sample is known, an exact probe can be synthesized. Lathe, R., *J. Mol. Biol.* 183, 1 (1985). A $^{32}$P-labeled DNA probe generated by nick translation can be hybridized to DNA fragments separated on an agarose gel and blotted onto cellulose nitrate. This process is known as southern blot hybridization. Wahl, G. et al., *Proc. Natl. Acad. Sci., USA* 76, 3683 (1979). Alternatively, the DNA sequence can be prepared by reverse transcription or by chemical synthesis.

The DNA sequence can be chemically synthesized if the amino acid sequence of an enzyme which catalyzes the production of melanins is known. Several prior art methods can be utilized to determine the amino acid sequence of the enzymes. A part of the amino acid sequence can be determined and used to prepare a primer for reverse transcription. The DNA sequence can code for the specific amino acid sequence of the enzyme. Alternatively, the DNA sequence can contain sequences which code for all or part of the enzyme. For example, the DNA sequence could code for the entire amino acid sequence of tyrosinase or it could code for a substantial portion of the amino acid sequence of tyrosinase. The DNA sequence could also code for a fusion protein which contains amino acids other than those which code for the enzyme. The tyrosinase gene has been cloned from *Streptomyces antibioticus* DNA by digestion with BclI. DNA fragments were ligated to BclI-cleaved pIJ37 or to BamHI-digested pIJ41. Ligation mixtures were then used to transform protoplasts of *Streptomyces lividans* 1326. Katz, E. et al., (1983), Supra. In addition, a tyrosinase gene can be isolated from any organism which produces melanin. Thus, the gene can be isolated from human hair follicles, melanocytes or melanomas, cuttlefish, red roosters, bacteria and fungi among others. For example, a human tyrosinase gene can be obtained as described in U.S. Pat. No. 4,898,814.

Transformation Vectors

The vectors of the present invention are vectors which contain DNA coding for enzymes which catalyze the production of melanins. The DNA may be native to the intended host or foreign DNA. Foreign DNA is DNA which is exogenous to or not naturally found in the organism to be transformed. It can be inserted into cloning vectors to transform a host organism. The foreign DNA of the present invention is derived from or has substantial sequence homology to DNA of organisms which naturally produce melanins. The vectors of the present invention are produced by standard techniques. Appropriate vectors which can be utilized as starting materials are known in the art.

The construction of the vectors can be performed in a suitable host, for example, *Escherichia coli*. A DNA sequence coding for enzymes which catalyze the formation of melanins, is obtained by conventional means and inserted into any vector suitable for the transformation of microorganisms.

The DNA sequence coding for the enzyme or part thereof is inserted into an appropriate vector in such a manner that the enzyme is correctly expressed. In other words, the DNA sequence is positioned in the proper orientation and reading frame so that the correct amino acid sequence is produced upon expression of the DNA sequence in the host. In accordance with conventional techniques, a chimeric DNA sequence is generally constructed which contains a promoter operable in the specific host microorganism and the DNA sequence coding for the desired enzyme. The chimeric DNA sequence may further contain 3' non-coding sequences operable in the host. The chimeric DNA sequence can be prepared in situ within a suitable vector by inserting the DNA sequence coding for the enzyme into a restriction site of a known host transformation vector. Alternatively, the chimeric gene could be first constructed and then inserted into a vector to produce a transformation vector. The vector can be further modified by utilizing an enhancer sequence and/or a strong promoter, which leads to an increased production of the enzyme.

The typical vector is a plasmid having one or more marker genes for antibiotic resistance, an origin of replication, and a variety of useful restriction sites for cloning or subcloning restriction fragments. A large number of vectors have been described which are useful for transforming many microorganisms including but not limited to Streptomyces and *E. coli*. See, for example, *Cloning Vectors*, Pouwels, P. H. et al. ed. Elsevier Science Publishers Amsterdam (1985).

A large number of naturally occurring Streptomyces plasmids have been described, many of which are conjugally proficient. Two such isolates, SLP1.2 and pIJ101, have formed the basis of a series of useful plasmid vectors. Thompson, C. J. et al., *Gene* 20, 51 (1982). The plasmids of the SLP1 family, of which SLP1.2 is the largest detected member, were discovered as autonomous replicons in *S. lividans* 66 after interspecific matings with *S. coelicolor* A3(2). The SLP1 replicon is integrated in the *S. coelicolor* genome but can be excised together with various lengths of neighboring DNA to become autonomous in *S. lividans*. The SLP1 plasmids exist stably at a copy number of 4-5 per chromosome in *S. lividans* and have a narrow host range.

The 8.9 kb plasmid pIJ101 was discovered in *S. lividans* ISP5434 (Kieser, T. et al., *Mol. Gen. Genet.* 185, 223 (1982)) but can be conjugally transferred to a wide variety of Streptomyces species. Derivatives (e.g. pIJ102) have been isolated from the plasmid which have similar properties but are smaller. Kieser, T. et al. (1982), supra. Plasmid pIJ101 has a copy number of 100-300 per chromosome equivalent in most hosts and a minimum replicon of less than 2.1 kb. Derivatives carrying drug-resistance determinants have been constructed to act as vectors, and a chimeric plasmid which can be used as shuttle vector between *E. coli* and Streptomyces is available.

The temperate phage φC31 has a wide host range within the streptomycetes and lysogenizes *S. coelicolor* A3(2) via a site-specific integration event. Lomovshaya, M. et al., *Bacteriol Rev.* 44, 206 (1980). Up to 42.4 kb of DNA can be packaged within a viable phage particle, but only 32 kb (at the most) of the DNA contains the genetic information essential for plaque formation. Derivatives of φC31 containing deletions can be used as vectors, and recombinant phages can either be grown lytically or used to lysogenize suitable streptomyces strains.

A limited number of genes cloned from various streptomycetes have been important in constructing vectors. The aminoglycoside phosphotransferase gene from *S. fradiae*, the aminoglycoside acetyltransferase gene (aac) from *S. fradiae*, and the ribosomal RNA methylase gene from *S. azureus*, that endows thiostrepton-resistance (tsr) have been used in pair wise combination to yield vectors allowing insertional inactivation. More recently, the tyrosinase gene, mel, whose product governs the synthesis of brown melanin pigments from tyrosine, have been cloned from *S. antibioticus* and used to construct vectors that allow a visual recognition of recombinants. Katz, E. et al. (1983), supra.

The plasmid vector pIJ702 is useful for generalized cloning of DNA into a wide range of Streptomyces, allowing a visual recognition of transformed colonies containing recombinant plasmids. The vector pIJ702 contains a thiostrepton-resistance determinant, tsr, for genetic selection and a tyrosinase gene, mel, whose product directs the synthesis of brown melanin pigments from tyrosine. Insertional inactivation of the mel gene leads to non melanin-producing transformants, whereas the intact mel locus yields dark brown colonies. Unique sites for BglII, SacI and SphI are present in the mel gene. The vector can also be used for cloning DNA fragments generated by KpnI or PstI, though without easy recognition of recombinants. Unique restriction sites for BamHI and XhoI are not available for cloning, and insertion at the unique ClaI site inactivates the tsr gene, eliminating the genetic selection. The copy number of the vector is 40-300.

The pIJ702 vector is comprised of a 1.1 kb BclI fragment from *S. azureus*, containing the tsr gene (Thompson et al. (1982), supra), two contiguous BclI fragments, occupying 3.0 kb, from the *S. lividans* plasmid pIJ102 (Kieser, T. et al. (1982), supra), and a 1.55 kb BclI fragment from *S. antibioticus* containing the mel gene.

pBR322-derived plasmids are very common for use in *E. coli* transformation. They possess a pair of antibiotic resistance genes which confer antibiotic resistance when *Escherichia coli* are successfully transformed. Typically the insertion of a DNA segment is made so that one of the antibiotic resistance genes is inactivated. Selection then is accomplished by selecting for *E. coli* exhibiting antibiotic resistance conferred by the second gene. Bolivar, F. et al., *Gene* 2, 95 (1977); and Sutcliff, J., *Proc. Natl. Acad. Sci., USA* 75, 3737 (1978).

Another example of transforming vectors is the bacteriophage. The M13 series are modified filamentous *E. coli* bacteriophage containing single stranded circular DNA. The M13 series carry the lacZ gene for β-galactosidase and will metabolize the galactose analog Xgal to produce a blue color. Placing a cloned insert into the polylinker sequence located in the amino terminus of the lacZ gene inactivates the gene. Microorganisms carrying an M13 with an inactivated lacZ (representing a cloned insert) are distinguishable from those carrying an M13 with an active lacZ gene by their lack of blue color. Messing, J. et al., *Proc. Natl. Acad. Sci., USA* 74, 3642 (1977); and Messing, J., *Methods in Enzymology*, Vol 101, 20 (1983).

Other transforming vectors are the pUC series of plasmids. They contain the ampicillin resistance gene and origin of replication from pBR322, and a portion of the lacZ gene of *E. coli*. The lac region contains a polylinker sequence of restriction endonuclease recognition sites identical to those in the M13 series. The pUC series have the advantage that they can be amplified by chloramphenicol. When a DNA fragment is cloned into the lac region the lac gene is inactivated. When *E. coli* containing a pUC plasmid with an inactivated lacZ gene is grown in the presence of isopropylthiogalactoside (IPTG) and 5-bromo-4-chloro-3-indolyl β-D-galactopyranoside (Xgal) its colonies are white. If it carries a pUC plasmid with an active lacZ gene its colonies are blue. Vieira, J. et al., *Gene* 19, 259 (1982). Bacteria are transformed by means conventional in the art.

Transformation of Microorganism

The genus Streptomyces is one of three aerobic genera of bacteria of the order Actinomycetales. Streptomyces are Gram-positive, mycelial, spore-forming bacteria. Several naturally occurring Streptomyces plasmids have been described. *Streptomyces lividans* TK64 has no tyrosinase gene and produces no melanin. The plasmid pIJ702 has the tyrosinase gene and is a high copy number plasmid. This results in at least a 3 times increase in tyrosinase production over strains having a tyrosinase gene on the chromosome. The plasmid pIJ702 has been used to transform *Streptomyces lividans* TK64 to a high potential for production of extracellular melanin. Transformation is carried out by means standard in the art. Similarly the tyrosinase gene can be used to transform a variety of microorganisms after insertion into vectors that are useful for transforming the various host microorganisms.

Bluescript (obtained from Stratagene, LaJolla, Calif.) is a pUC derivative having a β-galactosidase color indicator and a lac promoter. The Bluescript plasmid has been modified by inserting a tyrosinase gene. This modified plasmid was used to successfully transform *E. coli* which make pigmented colonies.

It was found that high levels of melanin production in *E. coli* require coexpression of the tyrosinase gene with an ORF 5' from the mel locus of *S. antibioticus*. The mel locus in pIJ702 contains both the ORF, designated ORF438 and the tyrosinase gene. The mel locus of *S. antibioticus* ATCC 8663 has a high degree of homology to the mel locus of *S. antibioticus* IMRU3720. *S. antibioticus* ATCC 8663 is a strain which is different than the *S. antibioticus* IMRU3720 strain used to produce pIJ702. Sequencing of the tyrosinase gene from *S. antibioticus* ATCC 8663 revealed several nucleotide differences from the *S. antibioticus* IMRU3720. A new previously undescribed sequence 3' to the tyrosinase coding region has been identified, cloned and sequenced. Portions of the 3' sequence act as a tyrosinase activator. The new 3' sequence contains putative open reading frames that encode functional proteins involved in melanogenesis.

A T7/*E. coli* tyrosinase expression system was used to clone and identify the *S. antibioticus* ATCC 8663 tyrosinase gene region. The T7/*E. coli* tyrosinase expression system offers many advantages over Streptomyces plasmid cloning, including; a higher rate of transformation, rapid melanin detection, subsequent ease of DNA extraction, and manipulations of subcloning, mapping and DNA sequencing.

The T7/*E. coli* tyrosinase expression system is a two plasmid T7 promoter/T7 polymerase system which uses a bacteriophage T7 promoter vector that directs selective transcription of cloned genes in host strains of *E. coli* that also produces T7 RNA polymerase. Tabor, S. et al., Proc. Nat'l. Acad. Sci. USA, 82, 1074 (1985).

Recombinant *E. coli* cells containing the induced tyrosinase gene produced melanin pigments on agar plates and in liquid culture when supplemented with copper and tyrosine. However, the expression of ORF438 was found to be required for high-level melanin production in *E. coli*. In addition, the presence of 3' regulatory sequences also enhances melanin production.

Transformed into *E. coli* K38 (pGP1-2), the plasmid pBGC620.3, for example, gives a chimeric, bi-cistronic transcript that uses a bacteriophage T7 ribosome binding site (RBS$_1$) for translation of ORF 438 and uses the authentic *S. antibioticus* RBS$_2$ for translation of tyrosinase. pGP1-2 encodes a T7 RNA polymerase that is driven by a P$_L$ promoter. When the promoter is activated by heat shock at 42° C. the induced T7 RNA polymerase selectively expresses genes cloned in pT7-7 behind the T7 promoter. pGP1-2 also contains a kanamycin resistance gene as a selectable marker. Double transformants harboring both plasmids were selected at 30° C. on Luria Broth (LB) agar plates with ampicillin and kanamycin at 100 μg/ml each.

Figure 4A:
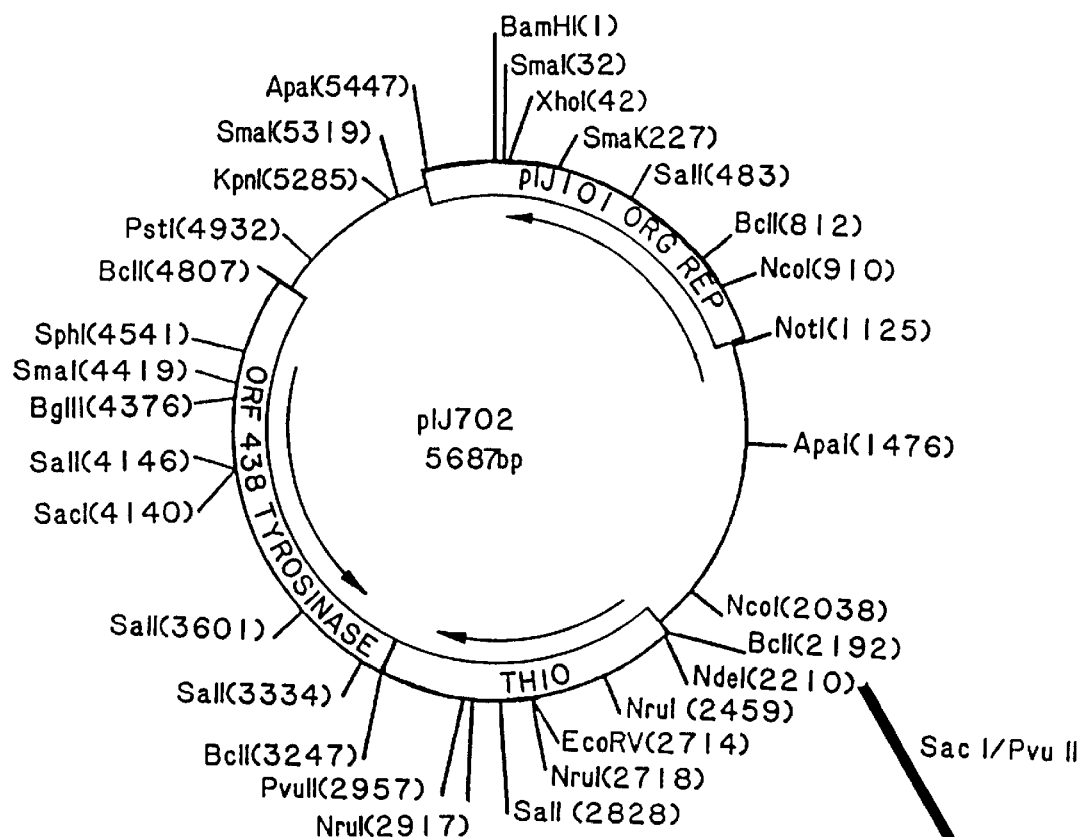
FIG. 4. Gene construction protocol for plasmid pBS1012.7.
Figure 4B:
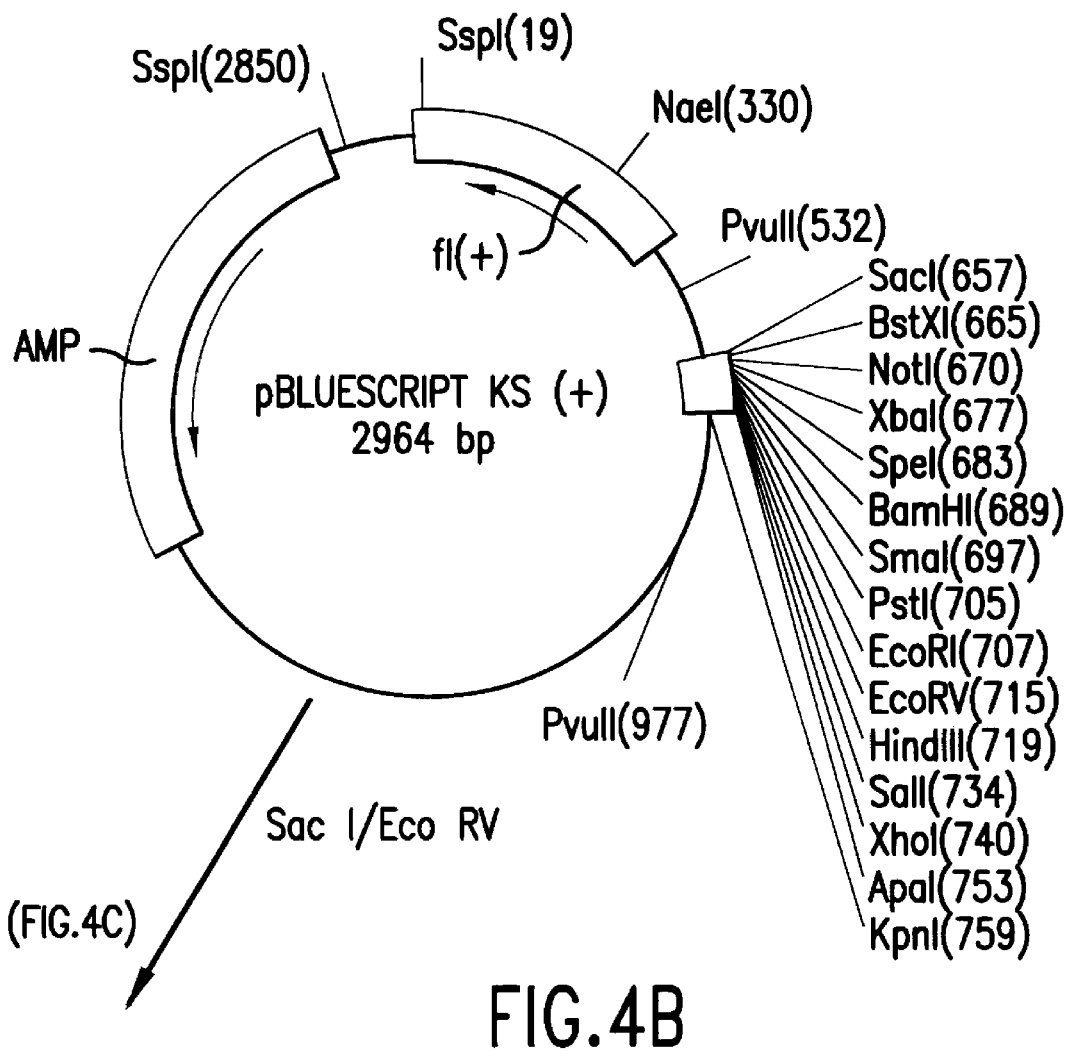
Figure 4C:
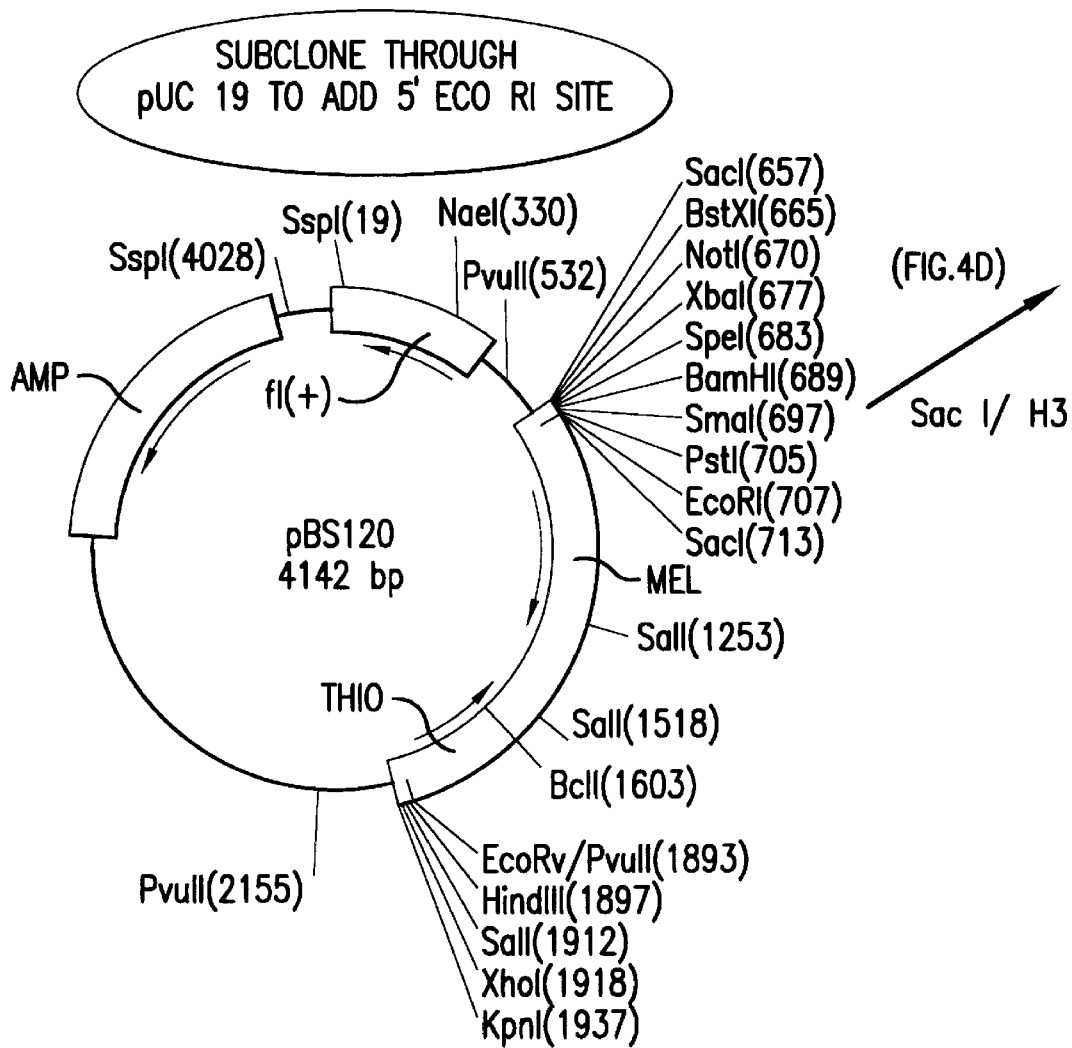
Figure 4D:
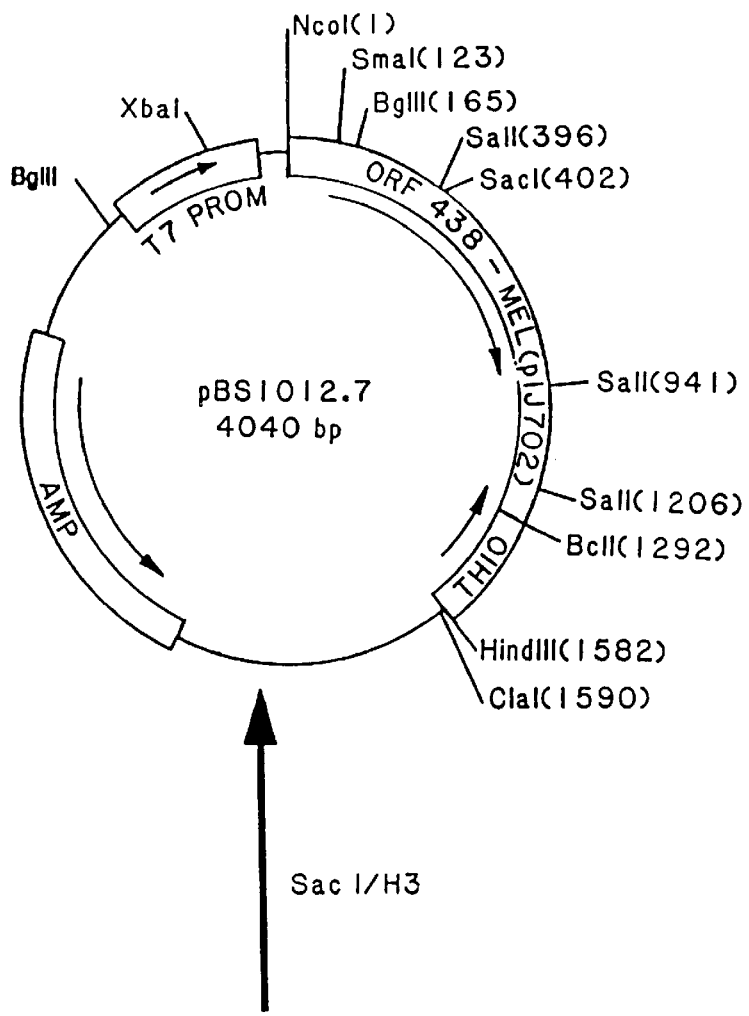
Figure 4E:
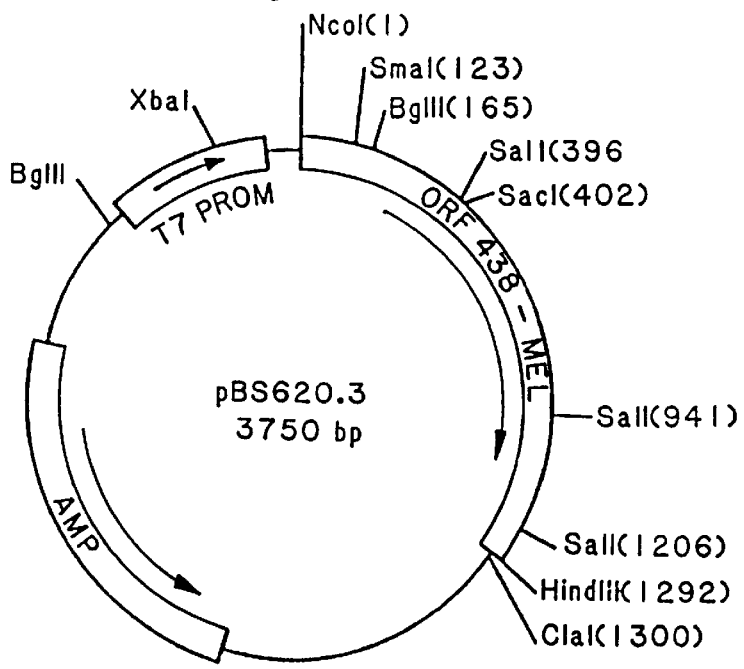
Figure 17:
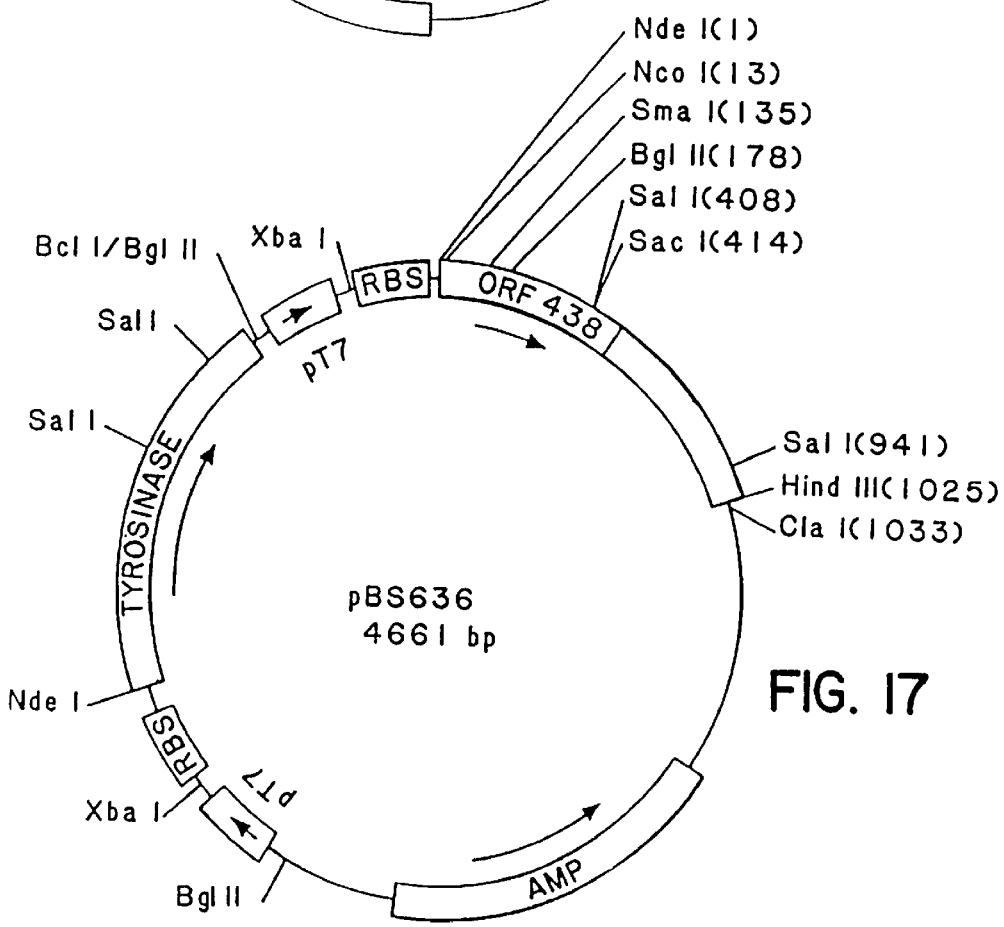
FIG. 17. Plasmid map of pBS636.

It has further been discovered that production of melanin in *E. coli* can be increased by placing the tyrosinase gene under the control of a T7 promoter and ribosome binding side and the ORF, such as ORF438, under control of a separate T7 promoter and ribosome binding site as shown in FIG. 17. In this arrangement, the production of melanin is increased at least four-fold, and possibly up to ten- to fifteen-fold, over melanin production with pBGC620.3 having the arrangement described above and shown in FIG. 4E.

It is possible, using the T7/*E. coli* tyrosinase expression system, to screen other precursor compounds, such as those listed above, for incorporation into melanin pigments. The resulting, melanin analogues are selected for unique colors and other chemical characteristics. It may be possible to screen for enhanced melanin production in the absence of added precursors to identify overproducing mutants in the amino acid biosynthetic pathways of *E. coli*. The ability to screen for a melanin phenotype in recombinant *E. coli* cells provides new opportunities for production of novel melanins and for protein engineering of tyrosinases with altered catalytic properties.

Mutagenesis

Mutations can be induced in microorganisms that are capable of producing melanins. The mutations can lead to a reduction, increase or no change in the production of melanins. Mutations are selected that lead to the enhanced production of melanins. The mutations can be induced by techniques known in the art which include radiation, such as ultraviolet light or gamma-radiations, as well as chemical mutagens such as ethidium bromide and ethyl methane sulfonate.

C. Purification of Melanins

Melanin has been purified from bacterial cells with 0.5N NaOH at room temperature and at 100° C. Pigmented fractions were found to be: (1) soluble in acid and base; (2) soluble in ethyl alcohol and base; and (3) soluble base only. Pavlenko, G. V. et al. (1981), supra.

Soluble melanin can now be extracted from the medium and purified. This can be done by first removing cells and particulate matter such as by filtration or centrifugation. If filtration is used, then a variety of filtration methods are known in the art including filtration through glass wool. If centrifugation is used, then 5,000×gravity is usually sufficient. The melanin is then precipitated at between pH 2–4, preferably about 3. Precipitated melanin is removed by either filtration or centrifugation. The melanin is washed by successive resolubilization at high pH, i.e. about pH 7.0 to about pH 9.0, preferably about pH 8.0, and precipitation at low pH followed by filtration or centrifugation. The melanin may also be concentrated using molecular weight filtration, such as reverse osmosis. Salt precipitation can be as effective in precipitating the melanin at low pH.

The invention is further illustrated by the following non-limiting examples.

Purification of Tyrosinase

Tyrosinase is secreted into the growth medium in Streptomyces cultures. Tyrosinase is retained intracellularly in *E. coli*. Intracellular tyrosinase can be purified from *E. coli* by standard procedures well defined in the literature. Sambrook et al. Molecular Cloning (1989).

Purification of ORF438 Protein

ORF438 protein is retained intracellularly in *E. coli* and is purified according to standard protocols. Further, purification is achieved through Fast Protein Liquid Chromatography (FPLC).

EXAMPLE 1

Purifications of Melanin

Melanin produced in the following examples was purified from the growth medium by the following procedure.

Cultures were filtered through glasswool to remove mycelium. Alternatively, particulate matter and cells were removed from the growth medium by centrifugation at 5,000×gravity. The pH of the melanin containing medium was then reduced to about 3.0 with HCl. The precipitated melanin was removed by centrifugation at 6,800×gravity. The precipitate was then removed and resolubilized at pH 8.0. The resolubilized melanin was washed by doubling the value of the liquid with sterile distilled $H_2O$. The process of precipitation, removal, resolubilization and washing was repeated 4 times in order to substantially remove any non-precipitable impurities. The product may be dried to completion in an oven at 200° C. for 48 hours, if desired.

EXAMPLE 2

Prior Art Melanin Production

Example 2 is set forth to show the prior art production of melanin. The method is taken from Hopwood, D. A. et al., "Genetic Manipulation of Streptomyces: A Laboratory Manual" The John Innes Foundation (1985).

Melanin production by *Streptomyces lividans* TK64 (pIJ702).

Preparation of Growth Medium

MMT MEDIUM was prepared from the following ingredients as described below.

MM MEDIUM:

| | |
|---|---|
| L-asparagine | 0.5 g |
| $K_2HPO_4$ | 0.5 g |
| $MgSO_4.7H_2O$ | 0.2 g |
| $FeSO_4.7H_2O$ | 0.01 g |
| $H_2O$ | 1000 ml |

The ingredients were dissolved in water, adjusted to pH 7.0–7.2 with NaOH, 100 ml placed into 500 ml flasks, and autoclaved for 20 minutes.

The following sterile stocks were prepared:

| | | |
|---|---|---|
| *Difco Casaminoacids (30%) (50x Stock) | | |
| *Glucose (50%) (50x Stock) | | |
| *$CuSO_4$.5 $H_2O$ (0.50%) (1000x Stock) | | |
| *Tyrosinase Inducer: | | |
| L-methionine (1%) | | |
| L-tyrosine (3%) | (33.3x Stock) | |
| L-leucine (5%) | | |
| *Tiger Milk: | | |
| L-arginine | (0.75%) | |
| L-cystine | (0.75%) | |
| L-histidine | (1.0%) | (133.3x Stock) |
| DL-homoserine | (0.75%) | |
| L-phenylalanine | (0.75%) | Does not dissolve |
| L-proline | (0.75%) | completely forms a |
| adenine | (0.15%) | white, milk-like |
| uracil | (0.15%) | solution |
| nicotinamide | (0.01%) | |
| thiamine | (0.01%) | |

*All of these stocks were autoclaved prior to making the medium.

The following ingredients were combined to prepare MMT medium:

100 ml MM MEDIUM 2 ml Casaminoacids 2 ml Glucose 750 ul Tiger Milk

For tyrosine and melanin production, the following ingredients were also included:

100 ul $CuSO_4.5H_2O$ 3 ml Tyrosinase Inducer

Inoculation and Growth of TK64 (pIJ702)

A small amount of the bacteria were scraped from the top of the plate and transferred into 10 ml of sterile water which was mixed and pipeted into six-500 ml flasks containing 100 ml of MMT. Cultures were grown at 30° C., and 120 RPM for 3 days.

Results

Melanin was extracted as described in Example 1. The yield of melanin was about 0.5 g/l, wet weight.

EXAMPLE 3

Enhanced Melanin Production by Modification of the Nitrogen Source

Preparation of Growth Medium

A medium was prepared containing 0.5 g/l $K_2HPO_4$, 0.2 g/l $MgSO_4$ $H_2O$, 0.01 g/l $FeSO_4$, 8 g/l casein hydrolysate, 0.3 g/l tyrosine 10 g/l glucose, 0.0005% $CuSO_4$ and 0.1 g/l L-methionine.

Inoculation and Growth of TK64 (pIJ702)

11 liters of the medium was inoculated with $1.4 \times 10^4$ spores/ml S. lividans TK64 (pIJ702) in 1 liter flasks containing 333 ml of growth medium. Cultures were grown for 3 days at 31° C. with shaking at 150 RPM.

Results

Melanin was purified as described in Example 1. A total of 1.58 grams per liter wet weight was obtained.

EXAMPLE 4

Enhanced Melanin Production by Removal of Carbohydrate Inhibitor

Preparation of Growth Medium

The medium preparation of Example 3 was repeated except that glucose was removed as a carbon source.

Inoculation and Growth of TK64 (pIJ702)

250 ml of medium in a 1 liter flask was inoculated with $5.8 \times 10^3$ spores/ml of S. lividans TK64 pIJ702. Cultures were grown at 30° C., with shaking at 170 RPM for 3 days.

Results

Melanin was purified as described in Example 1. 9 g/l wet weight of melanin was obtained.

EXAMPLE 5

Enhancement of Melanin Production With Casein Pentone Medium

Preparation of Growth Medium

The medium preparation of Example 4 was repeated except that casein hydrolysate (obtained from Sigma Chemical) was replaced by an equivalent amount of casein peptone and the L-methionine was removed.

Inoculation and Growth of TK64 (pIJ702)

Each 1 liter flask containing 250 ml of culture medium was inoculated with $5.8 \times 10^3$ spores/ml S. lividans TK64 (pIJ702). Cultures were incubated for 90 hours, at 30° C. with shaking at 150 RPM.

Results

Melanin was purified as described in Example 1 and 12 grams per liter, wet weight of melanin was obtained.

EXAMPLE 6

Enhancement of Melanin Production With Tyrosine

Preparation of Growth Medium

The medium preparation of Example 5 was repeated except that the quantity of casein hydrolysate was replaced by casein peptone and varying quantities of tyrosine were added. In different flasks the concentration of tyrosine in grams per liter was 0.3, 0.6, 0.9, 1.2 and 1.5.

Inoculation and Growth of TK64 (pIJ702)

Each 1 liter flask containing 250 ml of culture medium was inoculated with $5.8 \times 10^3$ spores/ml of S. lividans TK64 (pIJ702). Cultures were incubated for 90.5 hours, at 30° C. with shaking at 150 RPM.

Results

The optical density at 400 nm ($OD_{400}$) of cultures medium in the flasks was read at intervals. The average optical density after 90.5 hours of incubation was:

| Tyrosine in Grams/liter | $OD_{400}$ |
|---|---|
| 0.3 | 0.621 |
| 0.6 | 1.009 |
| 0.9 | 1.354 |
| 1.2 | 1.520 |
| 1.5 | 1.523 |

The melanin was purified as described in Example 1. The yield of melanin was 26 gram wet weight per liter of medium in the flask in which the tyrosine concentration was 1.5 g/l.

EXAMPLE 7

Production of Melanin In a Bioreactor

Preparation of Growth Medium

The growth medium was prepared as in Example 5. The medium contains 1.5 grams per liter of tyrosine. This medium contains no glucose or other carbon source except amino acids.

Inoculation and Growth of TK64 (pIJ702) Spore stock of S. lividans TK64 (pIJ702) was diluted 1:10 in water. A starter culture was produced by adding 50 μl of dilute spore stock to 250 ml of culture medium in a 1 liter flask. The starter culture was incubated at 30° C. with shaking until it reached mid-log phase.

Starter culture was then transferred to a 30 liter fermentor containing 20 liters of growth medium. Incubation was at 30° C. with constant mixing at 225 RPM until the maximum optical density of the medium was obtained at 400 nm ($OD_{400}$). Aeration during fermentation was by constant air flow at 1 liter of air per minute for 40 hours, and by 2.5 liters per minute for 40–60 hours, then by 3.0 liters per minute for the remaining 60–120 hours.

Results

Melanin was purified as described in Example 1. The yield of melanin was about 1.7 grams per liter dry weight.

EXAMPLE 8

Production of Melanin In A Bioreactor

Preparation of Growth Medium

The growth medium was prepared as in Example 5. The medium contains 1.5 grams per liter of tyrosine. This medium contains no glucose or other carbon source except amino acids.

Inoculation and Growth of TK64 (pIJ702)

Spore stock of S. lividans TK64 (pIJ702) was diluted 1:10 in water. A starter culture was produced by adding 50 μl of dilute spore stock to 250 ml of culture medium in a 1 liter flask. The starter culture was incubated at 30° C. with shaking until it reached mid-log phase. Starter culture was then transferred to a 42 liter fermentor containing 35 liters of growth medium. Incubation was at 30° C. with constant mixing at 225 RPM until the maximum optical density of the medium was obtained at 400 nm ($OD_{400}$). Aeration was by constant airflow at 1.5 liters of air per minute for 36 hours, 4.0 liters per minutes for 36–48 hours, and 5.0 liters per minute for the final 48–120 hours. Antifoam was added daily after 48 hours.

Results

Melanin was purified as described in Example 1. The yield of melanin was about 2.0 grams per liter dry weight.

EXAMPLE 9

Transformation of *Escherichia coli* to Melanin Production

Plasmid Construction

Figure 2B:
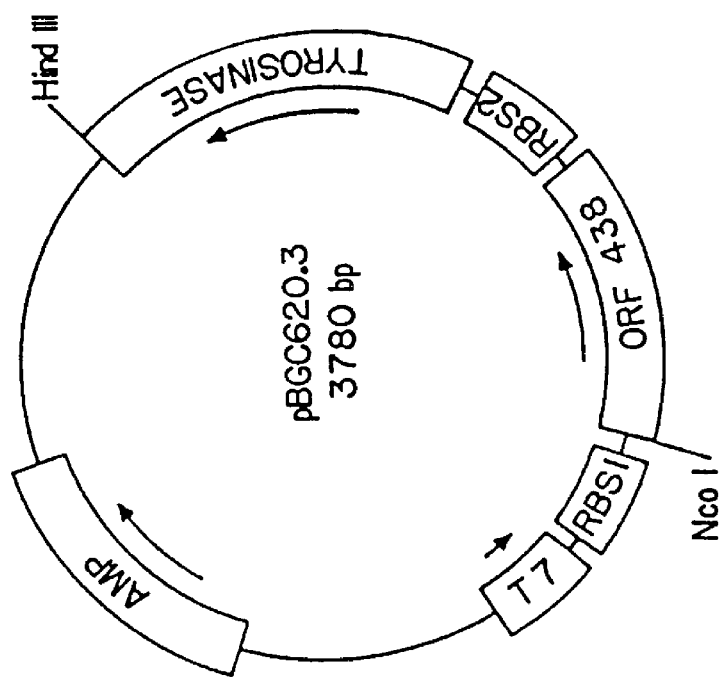
FIG. 2. *E. coli* expression plasmids containing tyrosinase (pBGC619) and ORF438 plus tyrosinase (pBGC620.3). The positions of the ampicillin resistance gene (AMP), T7 promoter (T7), and ribosome binding sites (RBS1 and 2) are shown in boxes. The vector sequence from RBS1 (underlined) through the first seven codons (uppercase) of tyrosinase (pBGC619) or ORF438 (pBGC620.3) is 5'aaggagatatacatATGGCTAGAATTGCCATGGCC-3'. The *S. antibioticus* sequence from RBS2 (underlined) through the ATG start codon of tyrosinase (pBGC620.3) is 5'-ggagcacccgcacATG-3'.
Figure 2A:
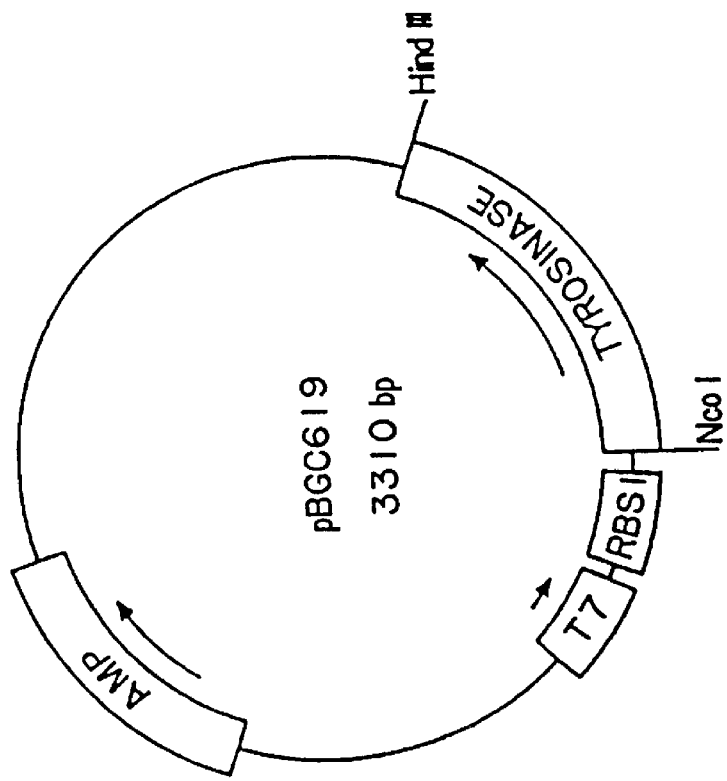

*Streptomyces lividans* carrying plasmid pIJ702 was obtained from the American Type Culture Collection. It carries the ATCC designation 35287. The ORF438 gene and the tyrosinase gene from the mel locus of *S. antibioticus* IMRU 3720 are contained on a 1291 base pair (bp) SphI/BclI fragment in plasmid pIJ702. Bernan, V. et al., (1985), supra. ORF438 and tyrosine were cloned into plasmid pT7-7 (obtained from S. Tabor) to make pBGC620.3. See FIG. 2. Plasmid pT7-7 is a derivative of pT7-5. Tabor, S. et al., *Proc. Natl. Acad. Sci.* USA 82, 1074 (1985). Plasmid pT7-7 has a T7 bacteriophage promoter, and a strong ribosome binding site upstream of the polylinker. It gives a fusion protein containing four extra amino acids at the N-terminus when the filled-in EcoR1 site is used.

The SphI site at the start codon of ORF438 was digested with mung bean nuclease and ligated to NcoI linkers (5'-dCAAGCTTG-3'). The BclI site at the TCA termination codon of tyrosinase was filled in using Klenow and ligated to HindIII linkers (5'-dCAAGCTTG-3'). pT7-7 was cut with EcoR1, filled with Klenow, ligated to NcoI linkers (5'-dCAAGCTTG-3'), and cut with HindIII. The 1307 bp NcoI/HindIII fragment encoding ORF438 protein and tyrosinase was ligated into pT7-7 to make pBGCG20.3.

ORF438 with NcoI linkers is thus expressed as a fusion protein with five extra amino acids at the N-terminus (NH2-Met-Ala-Arg-Ile-Ala-ORF438-COOH). Plasmid pBGC619 contains tyrosinase (without ORF438) cloned into pT7-7 as follows. An NcoI site was engineered by oligonucleotide mutagenesis at the ATG start codon of tyrosinase in plasmid pMa/mel#3 (M. Kumagai, unpublished). The tyrosinase coding region was then ligated as an NcoI/HindIII fragment into the modified McoI/HindIII pT7-7 vector (as above) to give pBGC619. See FIG. 2. Tyrosinase is thus expressed as a fusion protein in pBGC619 with five extra amino acids at the N-terminus (NH2-Met-Ala-Arg-Ile-Ala-tyrosinase-COOH). Plasmid pBGC620.2 is identical to pBGC620.3 except for a reading frame mutation in the ORF438 coding sequence. The reading frame assignments in all of these clones are consistent with the identified in vivo translation products as shown in FIG. 3A.

Expression

Plasmids pBGC619, pBGC620.2 and pBGC620.3 were transformed into *E. coli* strain K38 which harbors plasmid pGP1-2(Tabor et al. supra). pGP1-2 encodes a T7RNA polymerase that is driven by a $p_L$ promoter (Tabor et al. supra). When the promoter is activated (by a 42° C. heat shock) the induced T7 RNA polymerase selectively expresses genes cloned in pT7-7 behind the T7 promoter. pGP1-2 contains a kanamycin resistance gene as a selectable marker. Double transformants harboring both plasmids were selected on Luria broth (LB) agar plats (ampicillin and kanamycin at 100 µg/ml each) at 30° C. For melanin production on agar indicator plates (indicator plates were supplemented with $CuSO4.5H_2O$ (0.2 mM) and L-tyrosine (0.3 g/l)), colonies were grown overnight at 30° C., then 1 hr at 42° C., and followed by additional growth (3 hr to overnight) at 30° C. to allow for visible pigment formation. For melanin production in liquid culture, overnight cultures (30° C.) were diluted 1:50 into fresh LB and grown for 5 hr at 30° C., transferred to a 42° C. shaking water bath for 30 min, and then returned to 30° C. for continued overnight growth. Melanin production in liquid culture also required the addition of $CuSO4.5H_2O$ and L-tyrosine. Gels were incubated in Coomassie Brilliant Blue R (0.25%) in 50% methanol/10% acetic acid for 2 hours and destained overnight in 30% methanol/10% acetic acid.

Quantification of melanin production

Overnight cultures of *E. coli* K38/pGP1-2 harboring pT7-7, pBGC619, pBGC620.2 and pBGC620.3 were diluted into 50 ml of fresh LB broth and grown for 5 hours at 30° C. The cultures were transferred to a 42° C. shaking water bath for 30 min. . The cultures were returned to 30° C. $CuSO4.5H_2O$ (0.2 mM) and L-tyrosine (1.5 g/l) were added to the medium. The cultures were incubated for 24 hours.

Twenty four hour cultures were diluted 1:10 in water and read on a DMS 200 Varian scanning spectrophotometer with the pT7-7 vector control as blank. The cultures of *E. coli*/pBGC620.3 exhibited a black pigment. Diluted cultures exhibiting black pigment showed a broad absorbance profile between 400–700 nm that was nearly identical in all samples. Quantitation was measured at 670 nm.

Tyrosinase assay

Overnight cultures (as above) were diluted 1:50 into 50 ml of fresh LB broth and grown for 5 hours at 30° C. The cultures were then transferred to a 42° C. shaking water bath for 30 min and returned to 30° C. for 90 min. Aliquots of the culture (20 ml) were harvested by centrifugation at 6,000 g for 5 min.

For in situ assays of tyrosinase in *E. coli*, 100 mg wet weight of cells were washed and resuspended in 1 ml of 50 mM Hepes-KOH buffer (pH 6.8), 1 ml phenylmethylsulfonyl fluoride, and 1 ml of dithiothreitol. The cells were permeabilized by vortexing for 30 sec after the addition of 100 ul toluene:ethanol (1:4, v/v) as modified from Choudary *Anal. Biochem.* 138, 425 (1984). Aliquots (50 ul) of cells were then assayed at room temperature in 1 ml of 50 mM Hepes-KOH (pH 6.8), $CuSO4.5H2O$ (0.2 mM), and excess L-DOPA to saturation (18 mM). Oxidation of L-DOPA to dopachrome was monitored spectrophotometrically (DMS 200, Varian) at 475 nm over 10 min in matched quartz cuvettes. The reference cuvette contained the complete enzyme assay mix with pT7-7 vector-only cells. The amount of enzyme activity was calculated from the initial upward change in slope using a molar extinction coefficient for dopachrome of 3600. Lerch, K. et al., *Eur. J. Biochem* 31, 427 (1972). Specific activity is given in µmoles of L-DOPA oxidized per minute per 1 ml of cells. *E. coli* containing pBGC620.3 has a specific activity of 8.55. *E. coli* containing pBS1012.7 has a specific activity of 13.9. *E. coli* containing pBS1024 has a specific activity of 20.01.

**Lysozyme/Detergent Lysis of *E. coli* Cells**

Cell pellets of *E. coli* were suspended in 3–5 volumes ice cold 10 mM Tris-HCl (pH 7.4), 1 mM dithiothreitol (DTT), 0.1 mM phenyl methyl sulfonyl fluoride (PMSF), and 2 mg/ml lysozyme and incubated 20 min on ice. The suspended cells were then adjusted to 0.5% sodium deoxycholate and 0.1 mg/ml DNase I and incubated 30 min on ice. The suspended cells were then adjusted to 0.2% protamine sulfate and incubated 20 min at 4° C. with slow stiring. The cell debris was removed by centrifugation at –15,000 g for 15 min. The supernatant was adjusted to 60% saturation with ammonium sulfate (at 4° C. for one hour with slow stirring). The precipitated protein was removed by centrifugation at ~15,000 g for 15 min. The protein pellet was suspended in a small volume of buffer and aliquots were taken for tyrosinase enzyme assays using L-DOPA as substrate. The specific activity in the 60% ammonium sulfate fraction was 1.73 µmoles L-DOPA oxidized per minute per mg protein.

FIG. 3A shows an SDS-PAGE autoradiograph of proteins synthesized in vivo from T7 RNA transcripts (in the presence of rifampicin, only T7 RNA polymerase remains active). In pBGC619 a single protein band was observed at ~30 kD that corresponded to the expected size of tyrosinase (FIG. 3A, lane 1). The vector-only control produced no labeled proteins on the gel (FIG. 3A, lane 2).

For clones pBGC620.2 and pBGC620.3, identical tyrosinase bands were observed at ~30 kD in each case (FIG. 3A, lanes 3 and 4). The expression of tyrosinase in both of these clones was significantly reduced relative to pBGC619; this difference may reflect translational efficiency of RBS1 (from bacteriophage T7) versus RBS2 (from S. antibioticus). FIG. 3A also shows the ~12 kD out-of-frame translation of ORF438 (lane 3) and the full-length ORF438 protein of ~15 kD (lane 4) from clones pBGC620.2 and pBGC620.3, respectively. Clone pBGC620.3 which produced the correct size, full-length ORF438 protein of ~15 kD was found to be the superior melanin producer and also showed the highest levels of in vitro tyrosinase activity (see below). An additional clone pBS623 encodes ORF438 protein without tyrosinase. ORF438 protein is expressed to about 5% of total cell protein in E. coli transformants harboring pBGC620.3 or PBS623.

On Coomassie stained gels enhanced levels of tyrosinase relative to vector-only controls were not detected for any of the gene constructions (FIG. 3B). This is due in part to other endogenous proteins (29–30 kD) in E. coli that create a high background on the gels. In clone pBGC620.3, however, a major stainable protein band was observed at ~15 kD. that correspond to the full-length ORF438 protein (FIG. 3B, lane 4). The induced ORF438 protein expressed from pBGC620.3 was quantitatively the major protein in the cells.

High levels of melanin pigments accumulated only on plates containing clone pBGC620.3. As indicated by the autoradiographs above, this was the only clone that produced tyrosinase and a full-length ORF438 protein. Clone pBGC620.2 also showed minor amounts of melanin production after overnight growth but the levels were drastically reduced relative to pBGC620.3. Clones of pBGC619 and vector-only controls failed to show any melanin pigmentation after overnight growth on agar plates. The production of melanin from clone pBGC620.3 was dependent on the addition of copper and L-tyrosine to the agar plates.

A comparison of overnight growth following heat induction was performed for clone pBGC620.3 with L-tyrosine (A), N-acetyl-L-tyrosine (B), and L-tyrosine ethyl ester (C). Both of the tyrosine analogues produced strong pigmentation that ranged in color from yellow to various shades of brown. In addition, the development of an intense black melanin pigment from L-tyrosine in clone pBGC620.3 was greatly stimulated by the addition of ferric ion ($FeCl_3$) to the agar plate. With each of the substrates tested, the melanin pigments are visible in the E. coli colonies and in the surrounding agar medium. An E. coli control that lacks a functional tyrosinase gene did not produce any pigment.

Liquid cultures of pBGC620.3 also showed strong melanin pigmentation when heat induced and grown overnight at 30° C. in the presence of copper and L-tyrosine. The formation of melanin in liquid cultures of pBGC620.3 required 24–48 hours of incubation following heat induction for maximal production of pigment. Cultures of E. coli vector-only controls never showed any visible melanin after induction and overnight growth in the same medium.

The amount of melanin produced in E. coli cultures harboring the three different gene constructions described above was also measured. Clone pBGC620.3 was by far the superior melanin producer after heat induction and overnight growth in liquid culture (Table 1). This culture showed an intense black melanin phenotype and yielded an OD670 nm of 3.82 absorbance units over the vector control. The majority of the melanin absorbance at 670 nm was localized extracellularly in the growth medium. Melanin production was significantly reduced (to 8% of pBGC620.3 levels) in liquid cultures that made out-of-frame ORF438 protein with wild-type tyrosinase (pBGC620.2). We were unable to detect any melanin absorbance in overnight cultures that produced the tyrosinase fusion protein without the ORF438 sequence (pBGC619; Table 1). Longer term cultures of pBGC619, however, did show weak melanin pigmentation (>72 hrs after induction) that was above vector background (data not shown).

Intracellular tyrosinase activity was measured in cell pellets from heat induced liquid cultures of E. coli. The highest enzyme activities were found in cell pellets from clones pBGC620.2 and pBGC620.3 (Table 2). The relative levels of tyrosinase activity in these clones, however, was not proportionate to the final melanin yields (Table 1). The disparity between these two clones is thus attributable to the presence or absence of a functional ORF438 protein. Only very low levels of tyrosinase activity were detected in clone pBGC619 (Table 2), which did not show the melanin phenotype in liquid culture (Table 1) or on agar plates after overnight growth. We were unable to detect any background tyrosinase activity in pT7-7 vector control cells over the time course of the enzyme assay. In addition, none of the induced cultures had any detectable extracellular tyrosinase activity. Tyrosinase was measured at two hours after heat induction when enzyme activity was highest.

TABLE 1

Melanin production in liquid culture of E. coli at 24 hr after tyrosinase induction.

| Construct | OD670 nm[+] | Relative Absorbance |
|---|---|---|
| pT7-7 | 0.00 | — |
| pBGC619 | 0.00 | — |
| pBGC620.2 | 0.31 | 0.08 |
| pBGC620.3 | 3.82 | 1.00 |

[+]Cultures were diluted 1:10 in water and read against the pT7-7 vector control as a blank.

TABLE 2

Intracellular tyrosinase activity in liquid cultures of E. coli at 2 hr after heat induction.

| Construct | Tyrosinase[+] | Relative Absorbance |
|---|---|---|
| pT7-7 | 0.00 | — |
| pBGC619 | 0.79 | 0.070 |
| pBGC620.2 | 5.27 | 0.616 |
| pBGC620.3 | 8.55 | 1.000 |

[+]μmoles L-DOPA oxidized/min per 1 ml pelleted cells. Melanin yields in E. coli range from 0.2 g/l dry weight to 3.0 g/l dry weight.

EXAMPLE 10

Streptomyces antibioticus, ATCC8663, was grown in NZ amino medium, Katz, E. and Goss, W. A. Biochem. J. 73:458 (1959). Total nucleic acids were isolated by the method of Hopwood, D. A. et al., supra Example 2, (1985). S. antibioticus 8663 DNA was probed with the pIJ702 tyrosinase gene (1.5 Kb BclI fragment). Southern Blot Analysis revealed that many restriction sites and DNA fragment sizes were conserved between S. antibioticus tyrosinase genes.

Southern blot data also indicated that a 6–8 Kb SacI/BamHI fragment could be cloned from the S. *antibioticus* 8663 genome and this fragment contains the 3' end of an ORF438 like sequence, the complete 8663 tyrosinase coding sequence and 6 Kb of DNA, 3' to the tyrosinase coding sequence.

pBS620.3 (formerly named pBGC620.3) was modified to make pBS1012.7 by inserting a BclI site near the 3'end of the tyrosinase (pIJ702) gene. See FIG. 4. The 890 bp SacI/BclI fragment from pBS1012.7, containing the 3' end of ORF438 and the entire pIJ702 tyrosinase, was removed.

Figure 5:
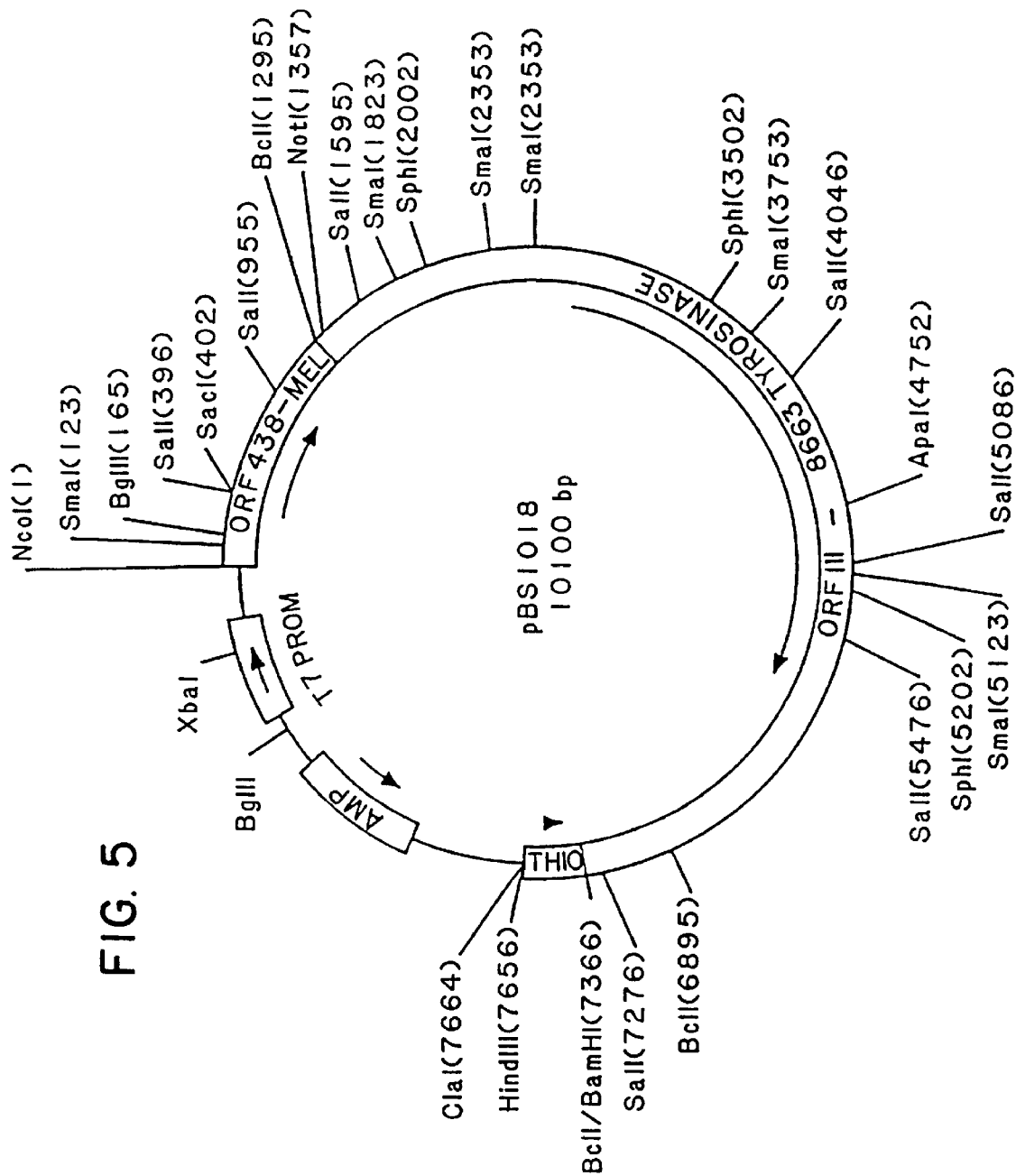
FIG. 5. Plasmid map of pBS1018.
Figure 6B:
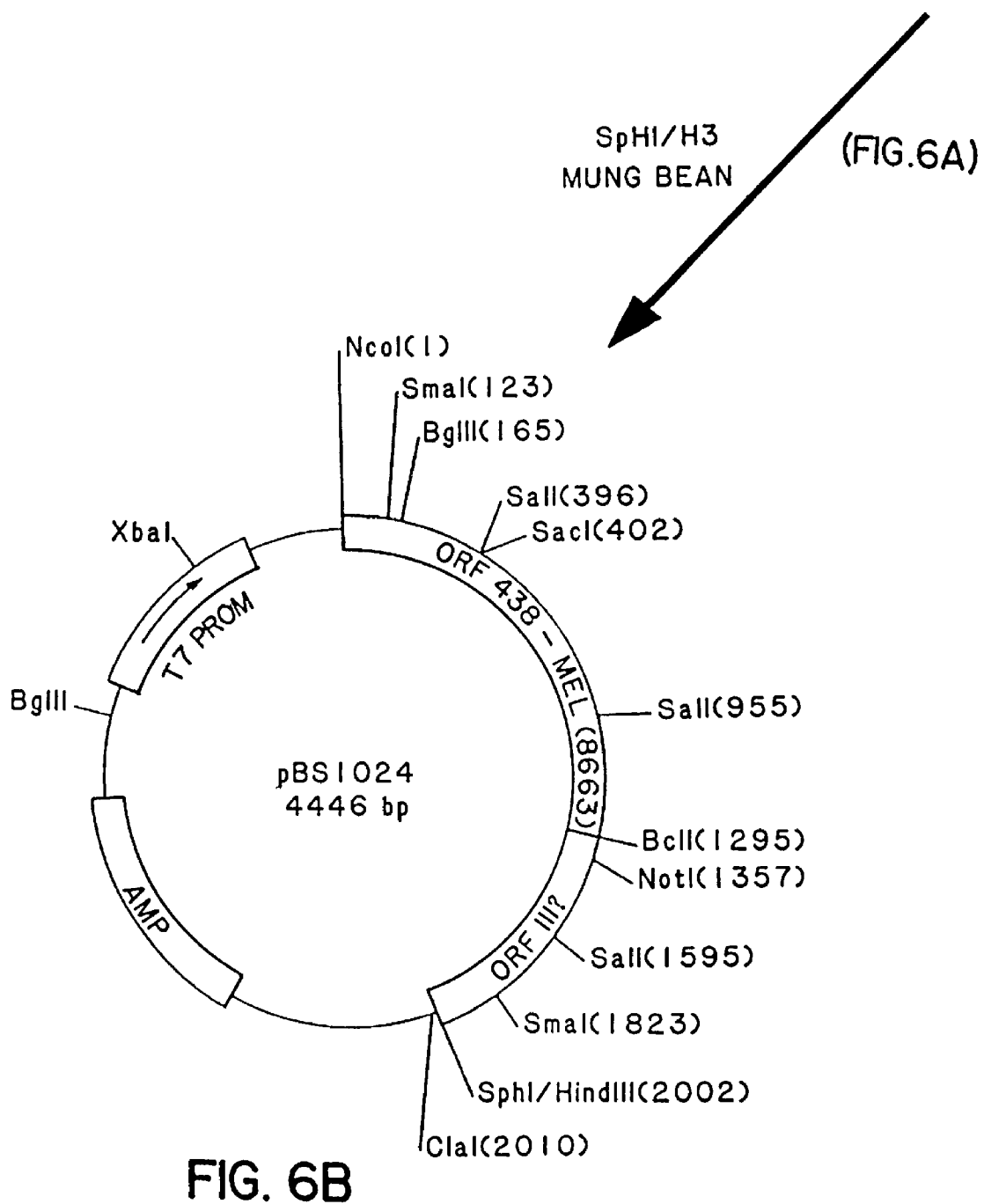
FIG. 6. Gene construction protocol for plasmid derivatives of pBS1018 and pBS1012.7 (pBS1022, pBS1024, pBS1025, and pBS1026).
Figure 6D:
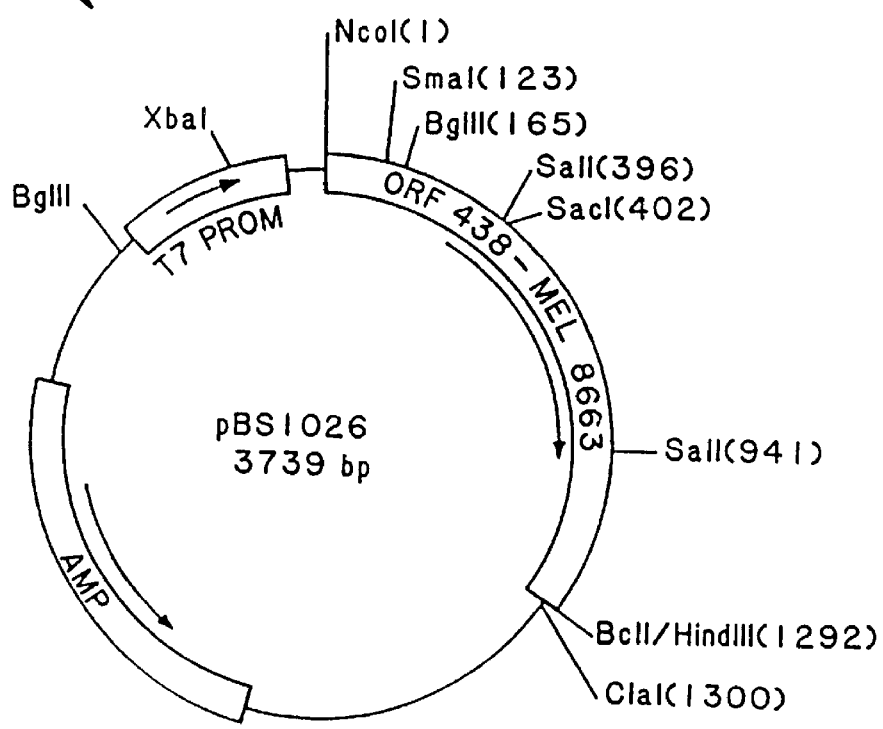
Figure 6E:
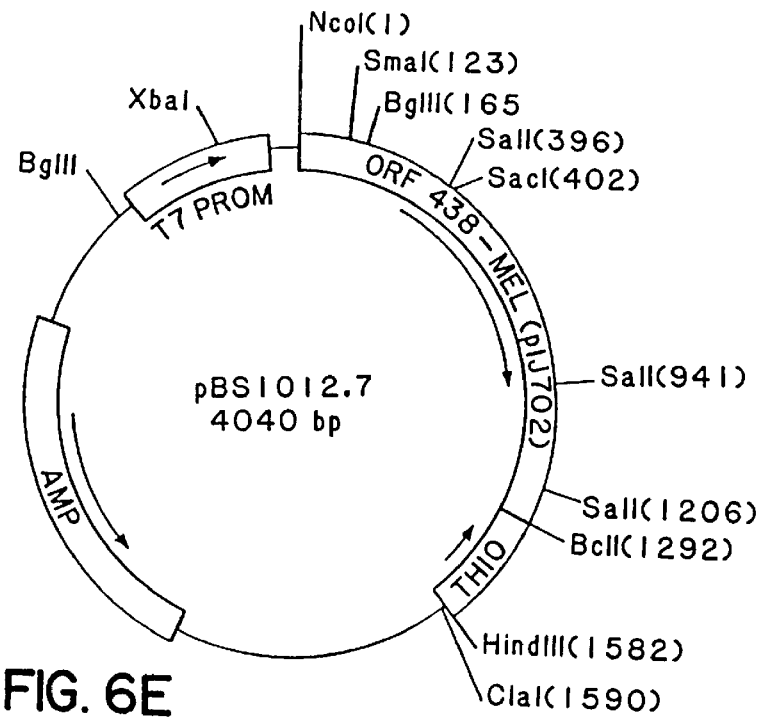
Figure 6F:
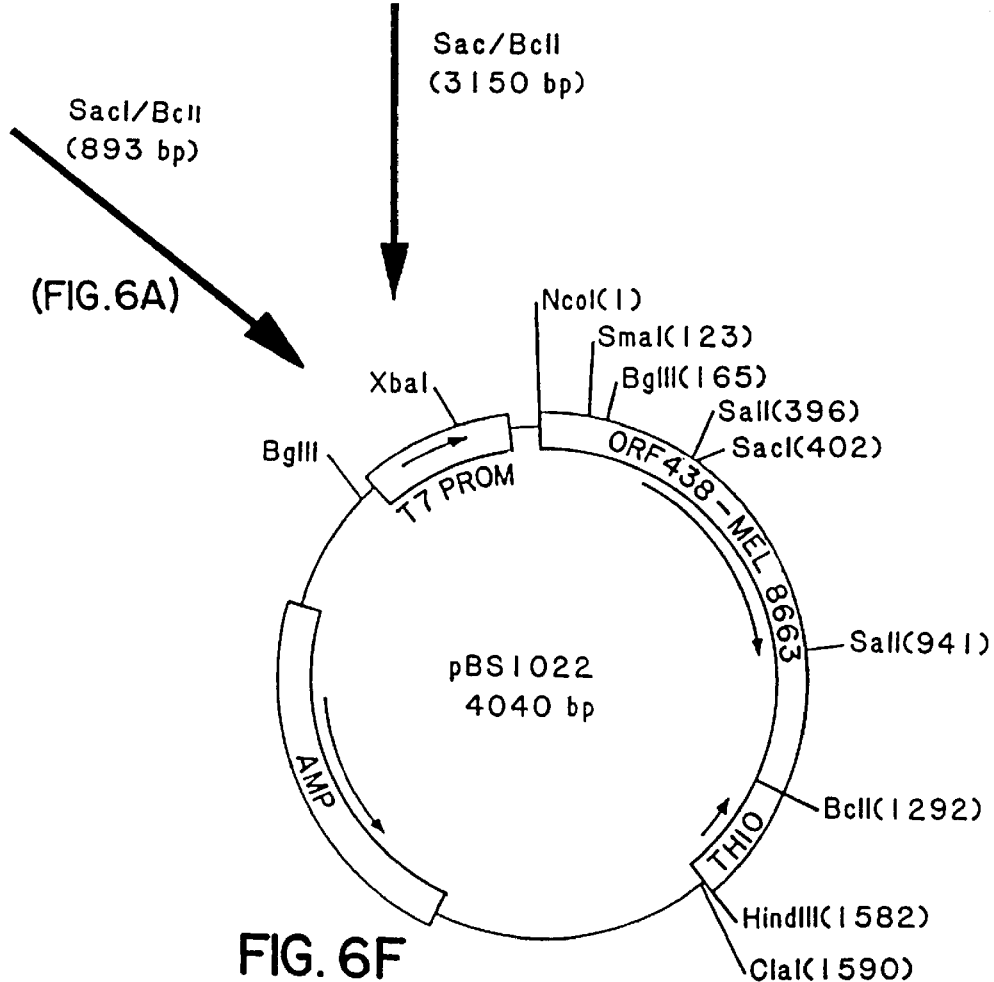

S. *antibioticus* 8663 chromosomal DNA was digested with SacI/BamHI and DNA fragments 6–8 Kb in length were recovered from low melt agarose. The SacI/BamHI fragment was ligated to pBS1012.7 from which the 890 bp fragment had been removed and transformed into E. *coli* C-600. Plasmid DNA from transformed E. *coli* C-600 was transformed into E. *coli* K38 (pGP1-2). The transformed E. *coli* were plated and grown up overnight at 30° C., heat shocked at 42° C. for 1 hr, then incubated at 30° C. A clone which produced melanin was designated pBS1018 which contains a hybrid between ORF438 from S. *antibioticus* IMRV 3720 and an ORF438-like sequence from S. *antibioticus* ATCC 8663. Plasmid mapping of pBS1018 (FIGS. 4 and 5) indicates that the 8663 tyrosinase gene is different (loss of a SalI site 85 bp from the BclI site and stop codon) from the pIJ702 tyrosinase. Also, 6 kb of DNA 3' to the tyrosinase gene was cloned as predicted. Several deletions or subclones of pBS1018 (FIG. 6) were prepared (pBS1022, 1024, 1025 and 1026) to study the effects that various lengths of tyrosinase 3' DNA would have on melanin yield and tyrosinase expression.

Figure 7:
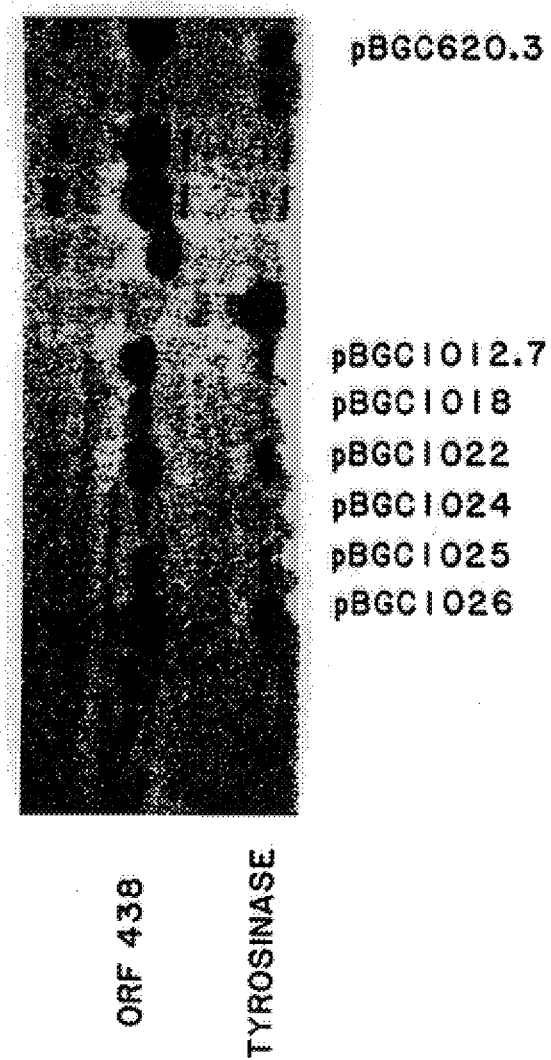
FIG. 7. SDS-PAGE of transformed *E. coli* cells producing tyrosinase and ORF438.

Liquid cultures of E. *coli* K38/pGP1-2 harboring pBS1012.7, pBS620.3, pBS1018, pBS1022, pBS1024, pBS1025 or pBS1026 were heat shocked [induced] at 42° C. and pulse labeled with [$^{35}$S] methionine. FIG. 7 shows the presence of protein bands at ~30 KD and ~15 KD, the expected size of tyrosinase and ORF438 protein, respectively, from each of pBS1012.7, pBS1018, pBS1022, pBS1024, pBS1025 and pBS1026.

Figure 8:
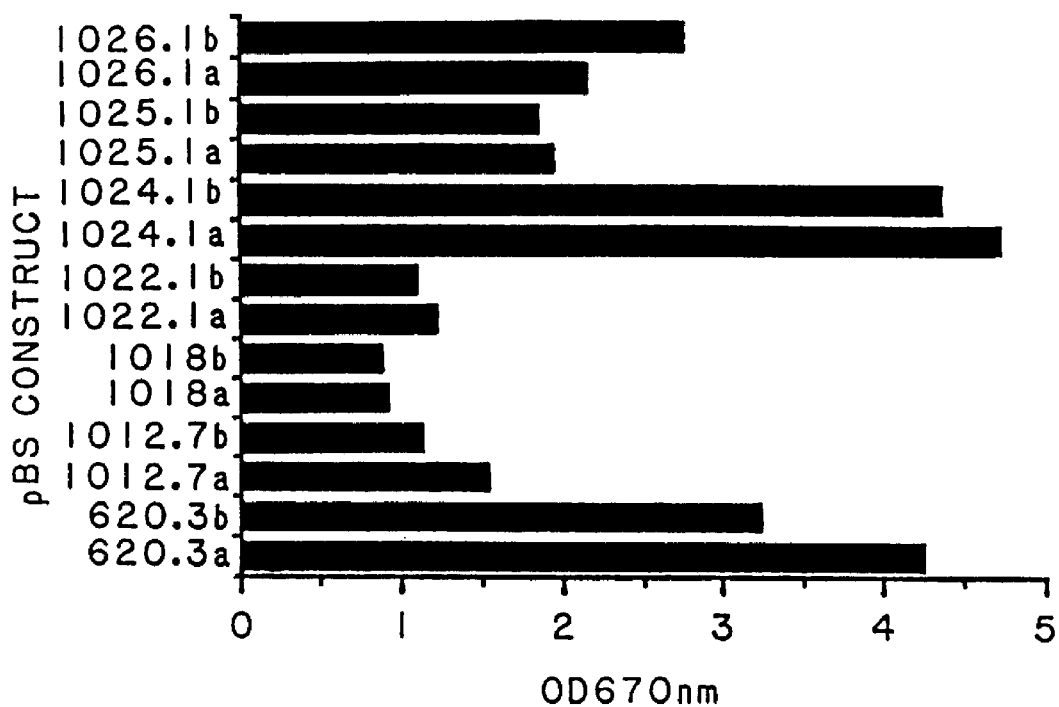
FIG. 8. Melanin production in transformed *E. coli* cells.
Figure 9:
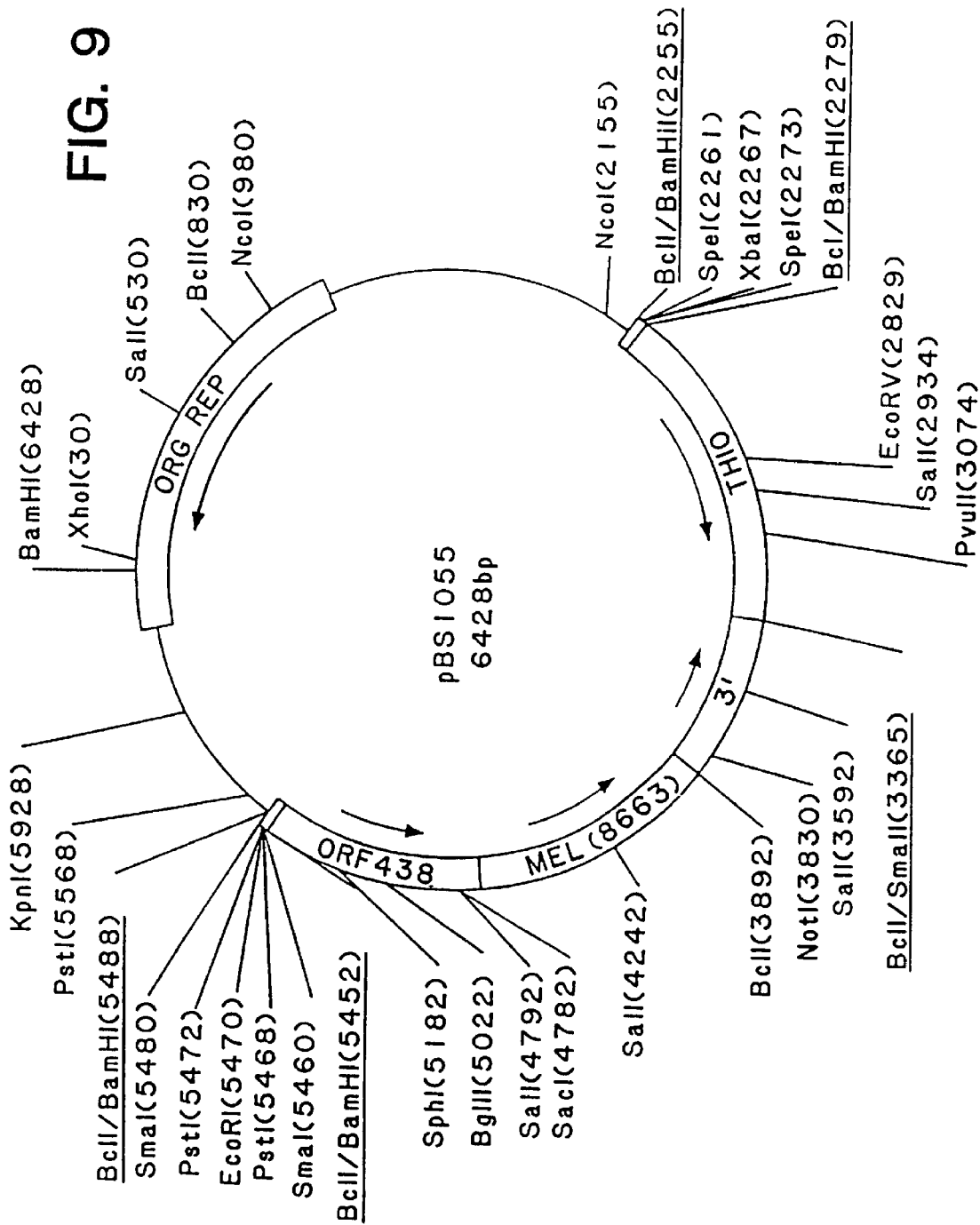
FIG. 9. Plasmid map of pBS1055.
Figure 10:
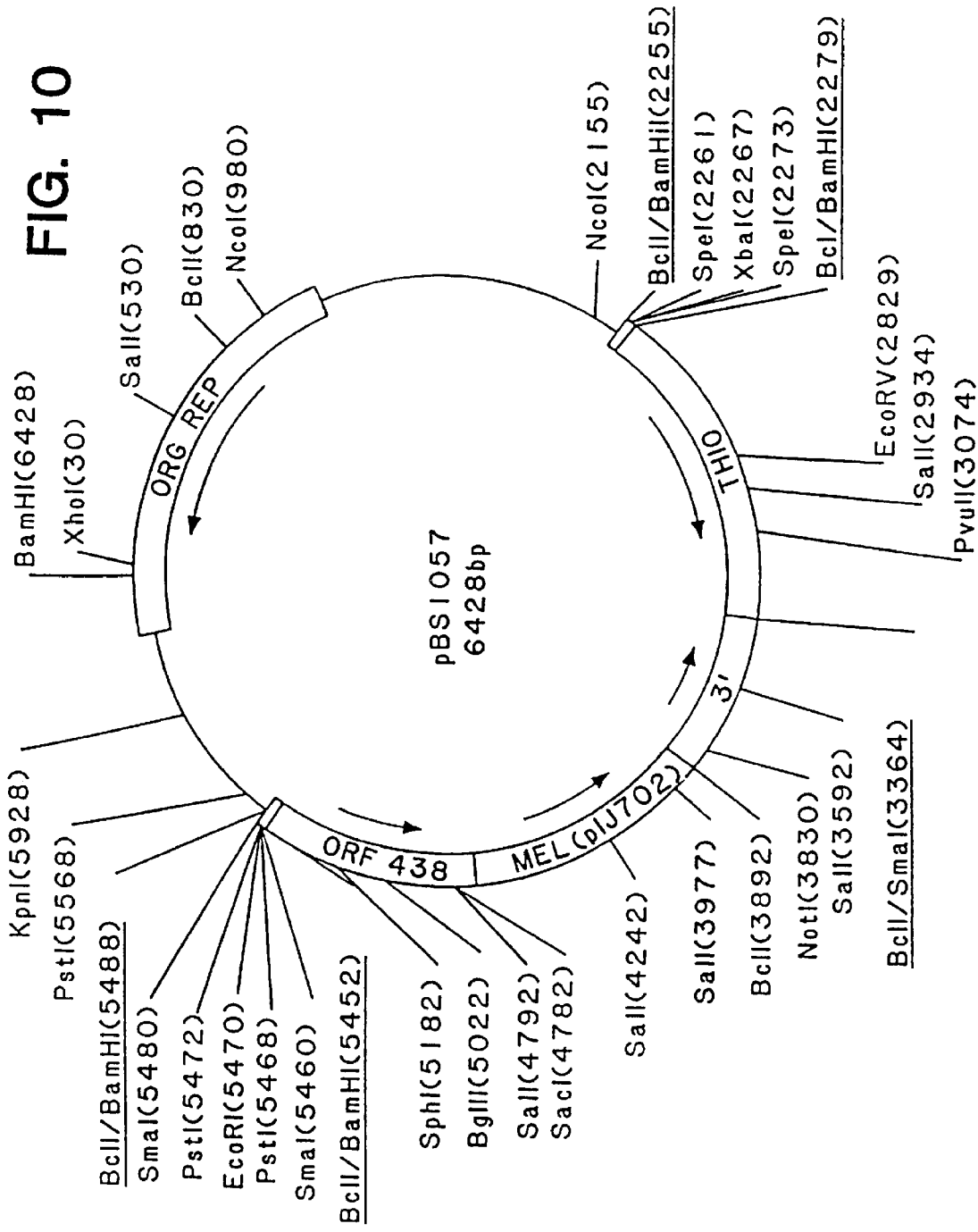
FIG. 10. Plasmid map of pBS1057.
Figure 11A:
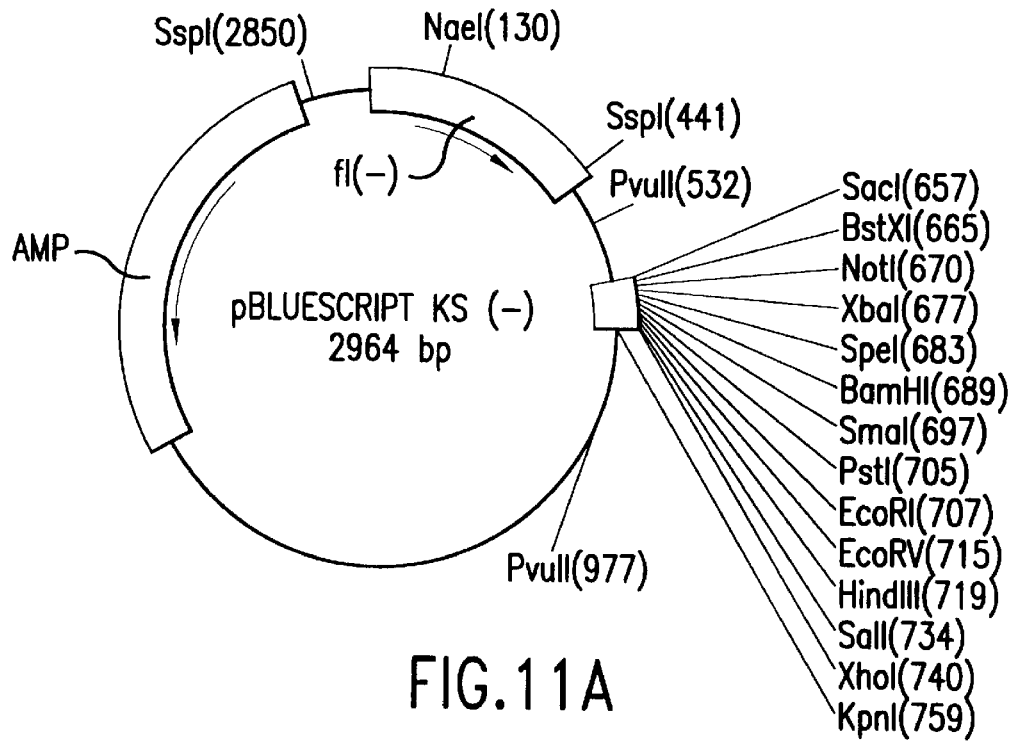
FIG. 11. Shows the construction of pBS115.
Figure 11B:
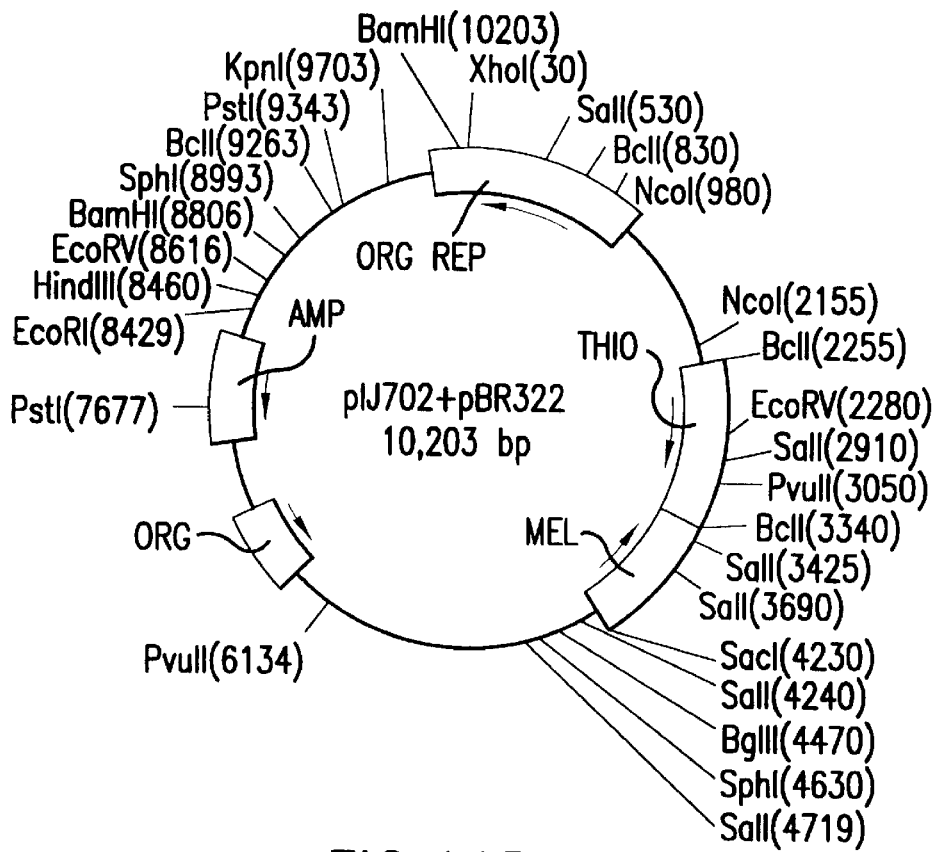
Figure 11C:
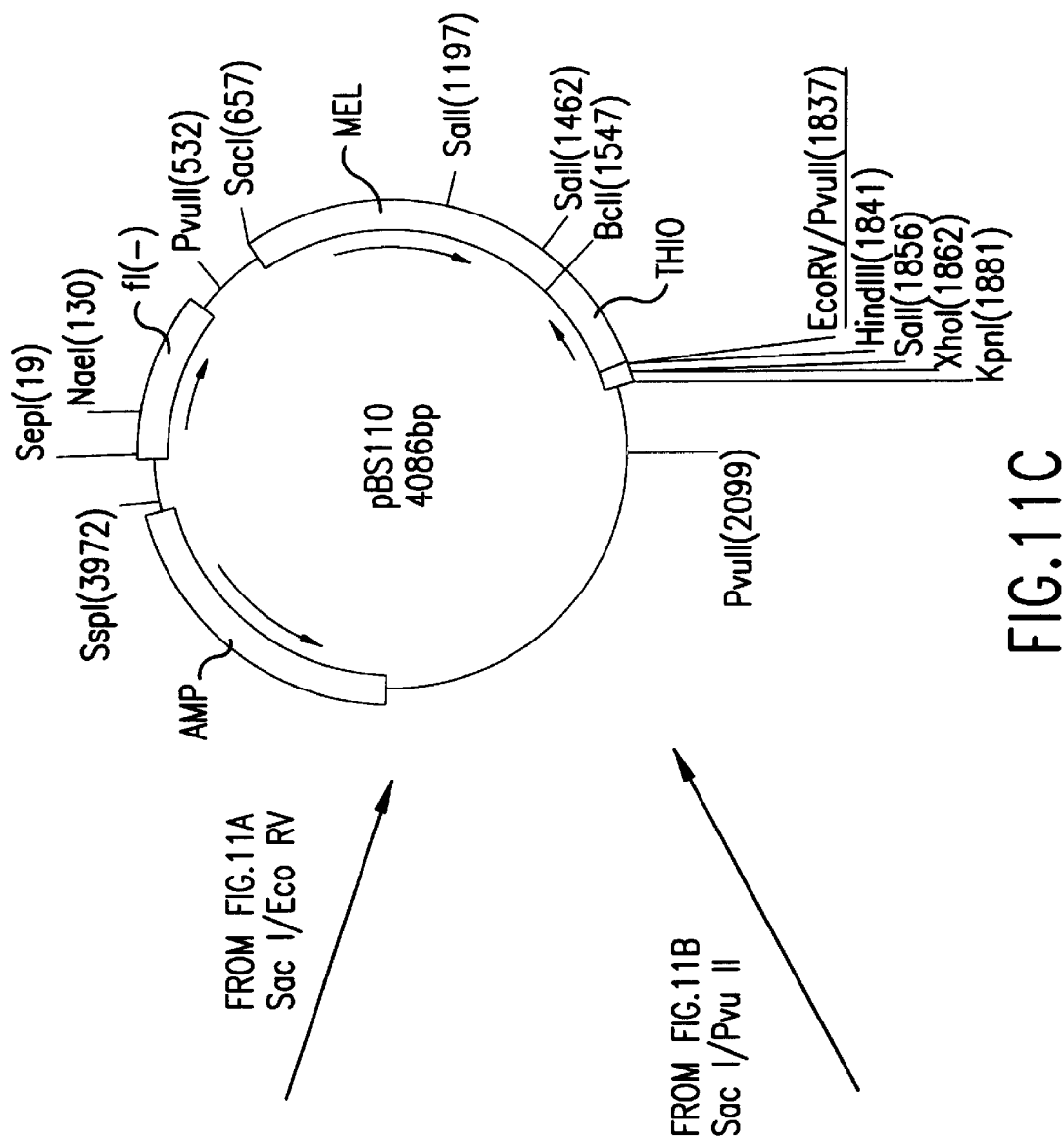
Figure 11D:
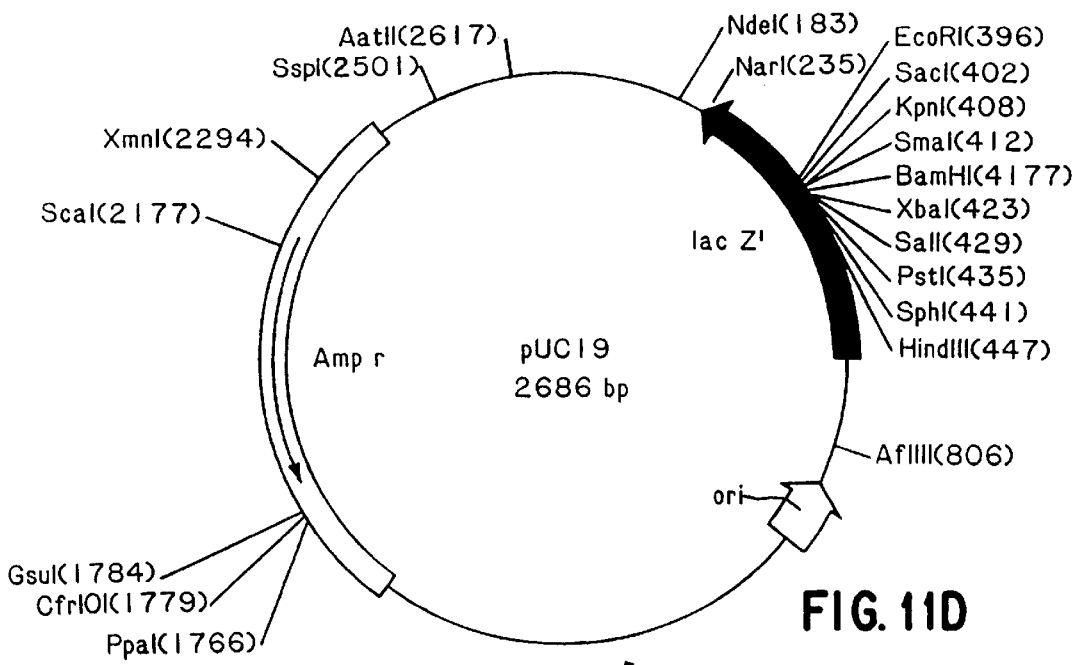
Figure 11E:
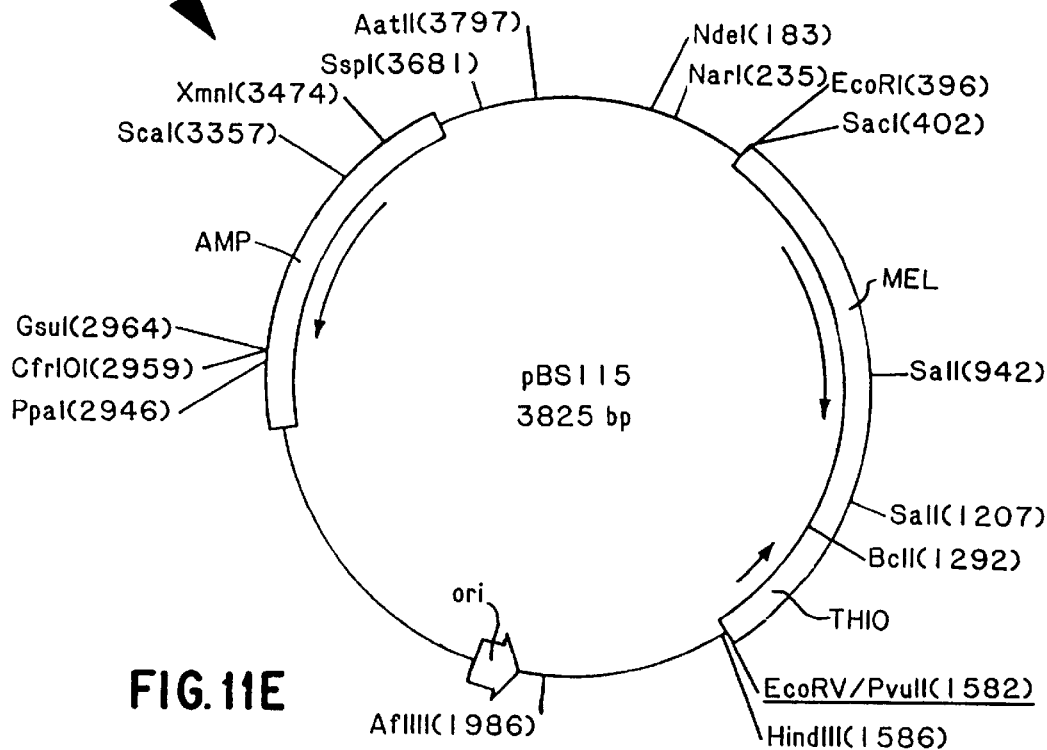
Figure 12A:
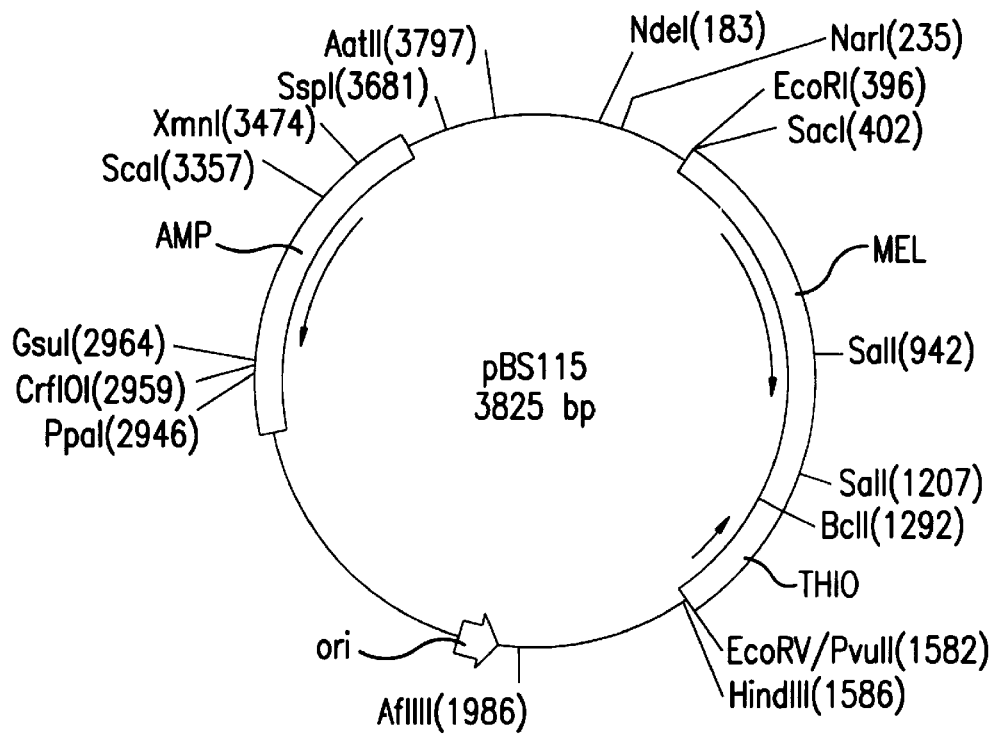
FIG. 12. Shows the construction of pBS130.
Figure 12B:
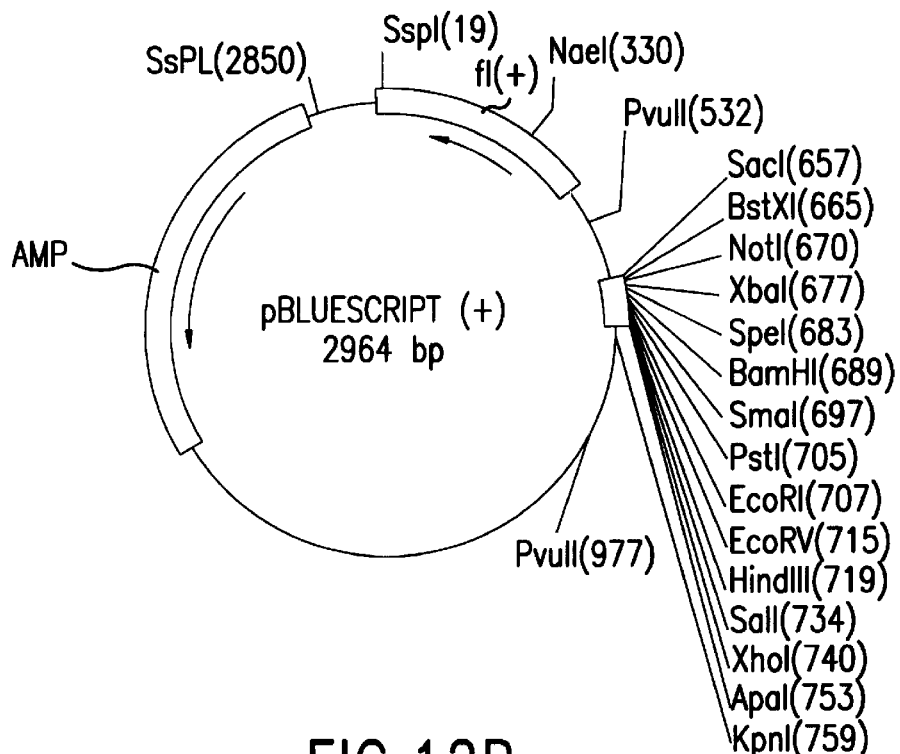
Figure 12C:
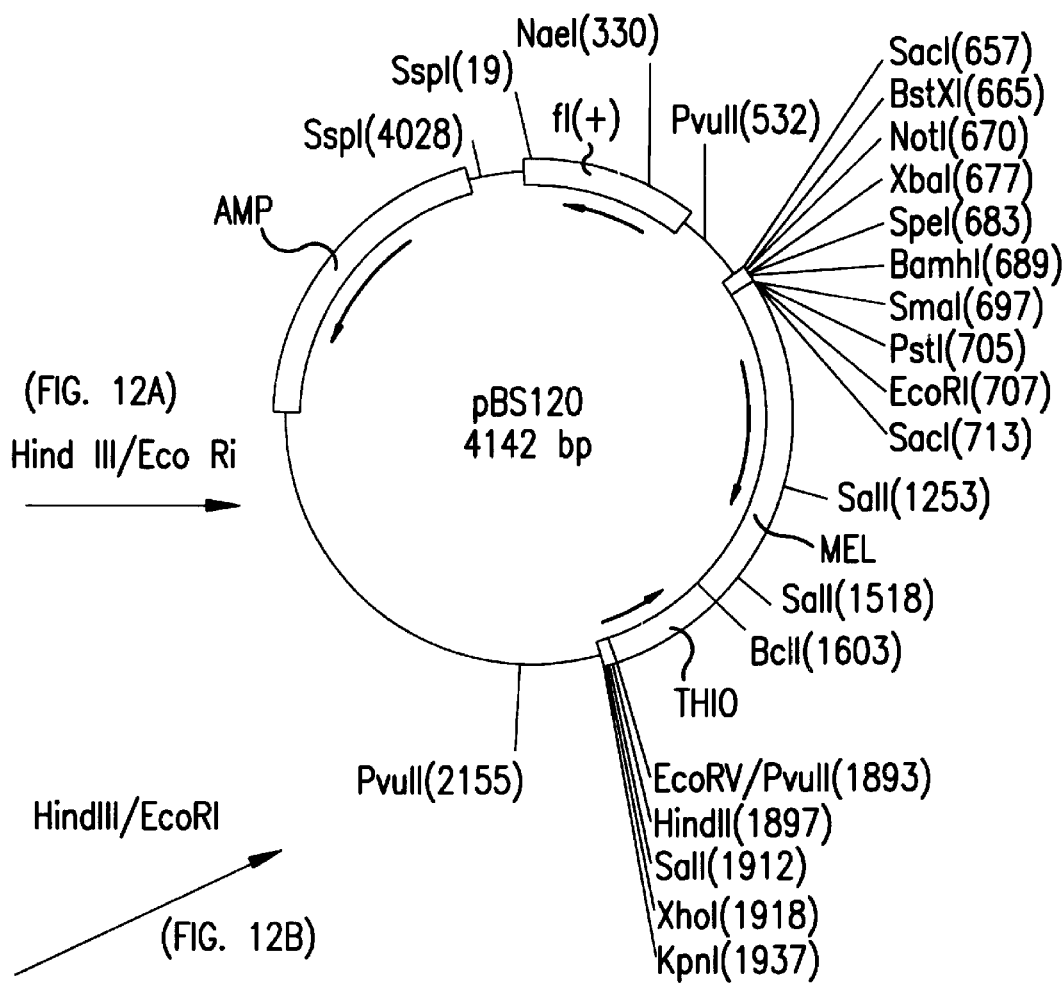
Figure 12D:
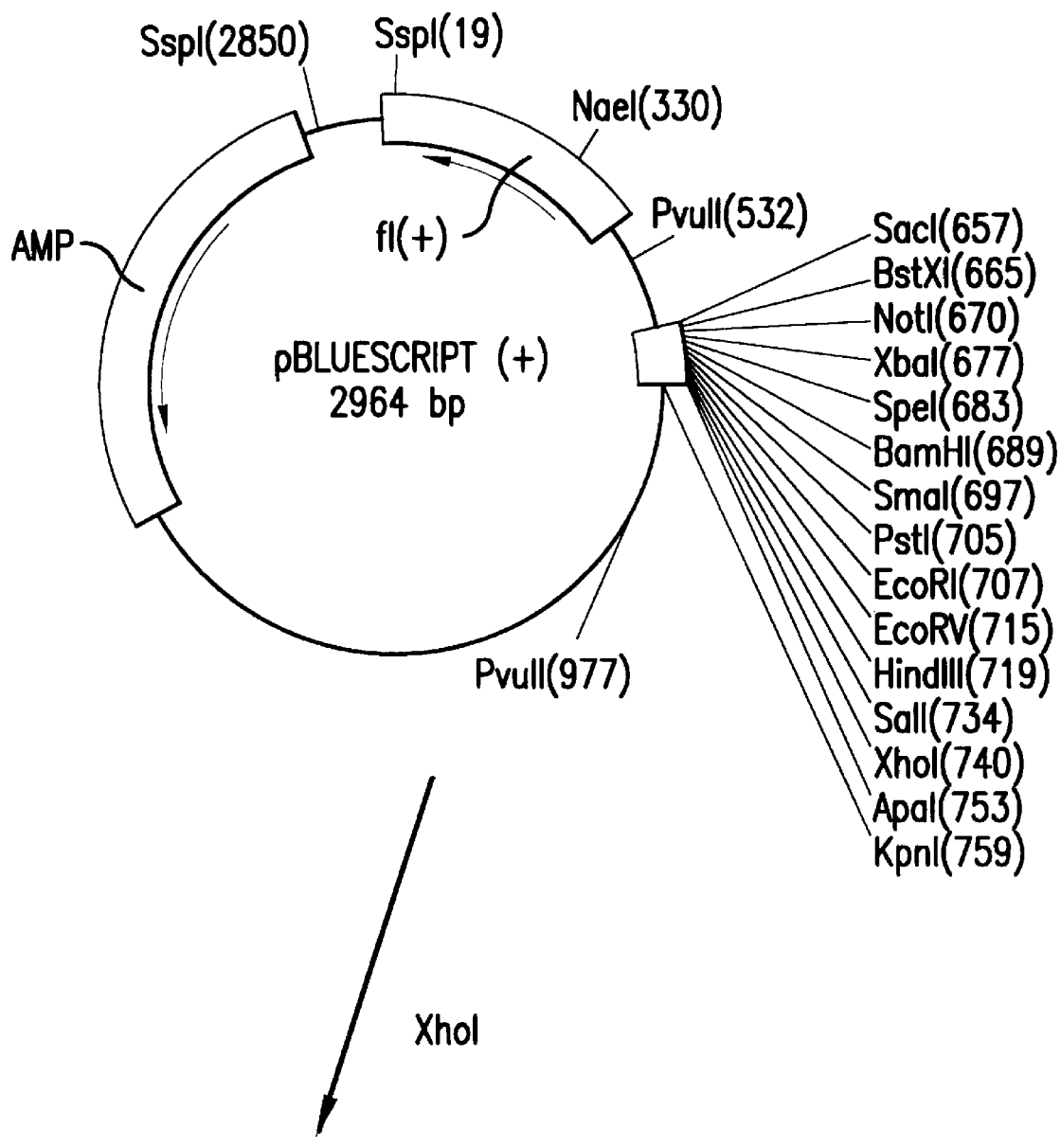
Figure 12E:
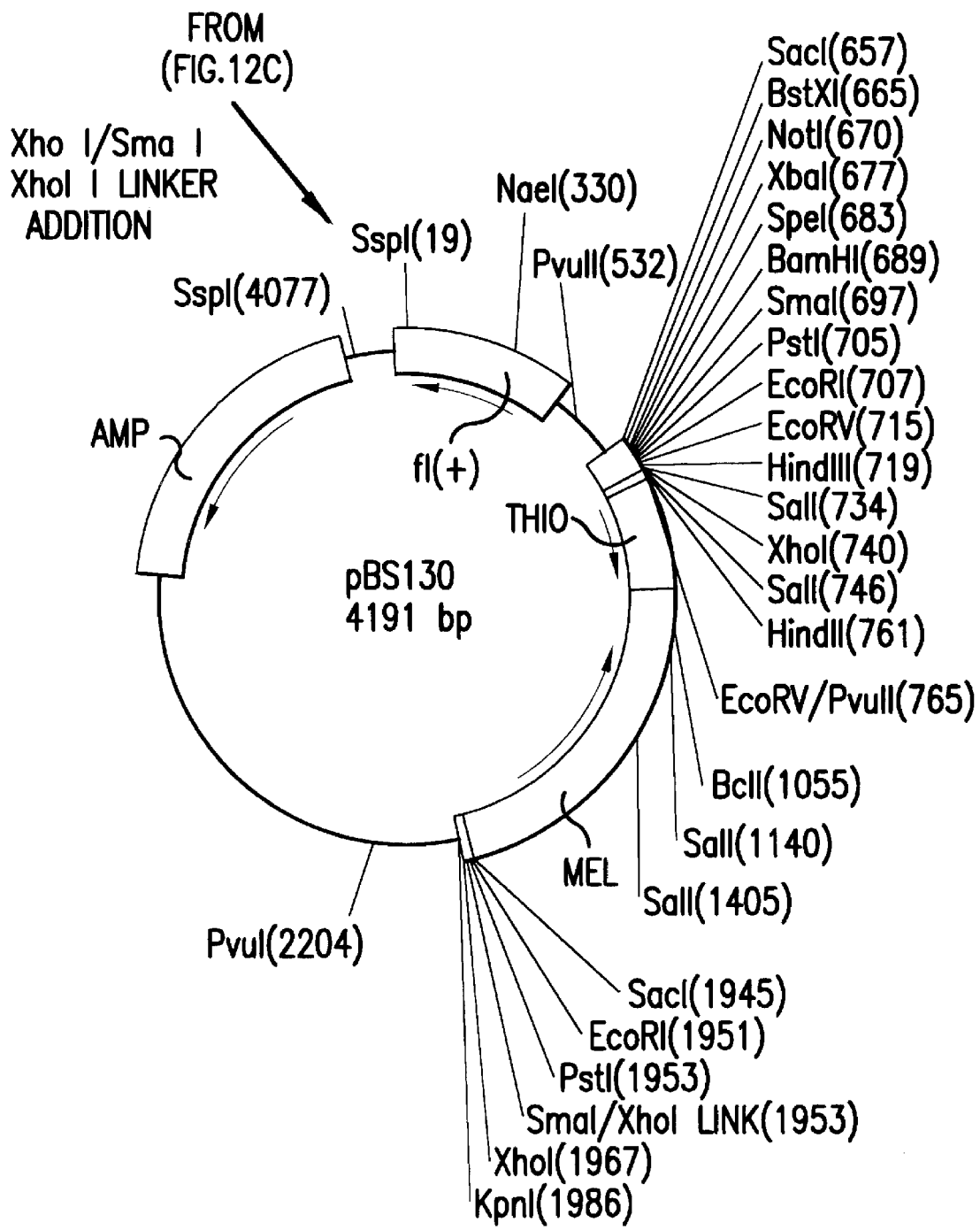

Melanin pigmentation in heat induced liquid cultures was determined by $OD_{670}$nm. pBS1024 was determined to be the superior melanin producer. pBS620.3 was used as the control. See FIG. 8. Melanin production in pBS1024 ranges from 0.2 g/l dry weight to 3.0 g/l dry weight depending on the precursors used.

EXAMPLE 11

E. *coli* K38 (pGP1-2)/pBS1024 or pBGC620.3 was grown in liquid medium supplemented with N-acetyl-L-tyrosine. A pink pigment was isolated from the growth medium.

EXAMPLE 12

E. *coli* K38 (pGP1-2)/pBGC620.3 or pBS1024 was grown in liquid medium supplemented with L-tyrosine ethyl ester. A yellow pigment was isolated from the growth medium.

EXAMPLE 13

E. *coli* K38 (pGP1-2)/pBGC620.3 or pBS1024 was grown in liquid medium supplemented with N-acetyl-L-tyrosine until the pigment became green. The green pigment was isolated from the growth medium.

EXAMPLE 14

Preparation of pBS636

Plasmid pBS130 was prepared as shown in FIGS. 11 and 12. Briefly, pIJ702 was cloned into pBR322 to produce pIJ702+BR322. This plasmid was digested with SacI and PvuII and the fragment containing the mel gene was isolated. pBluescript KS(−) was digested with SacI and EcoRV, the large fragment isolated and ligated with the SacI/PvuII fragment of pIJ702+pBR322 to produce pBS110. The SacI/PvuII fragment containing the mel gene was isolated from pBS110 and ligated to the large SacI/PvuII fragment from pUC19 to produce pBS115. The HindIII/EcoRI fragment containing the mel gene was isolated from pBS115 and ligated to the large HindIII/EcoRI fragment from pBluescript KS(+) to produce pBS120. The XhoI/SmaI fragment containing the mel gene was isolated from pBS120, XhoI linkers added, digested with XhoI and cloned into the XhoI site of pBluescript KS(+) to produce pBS130.

Figure 16:
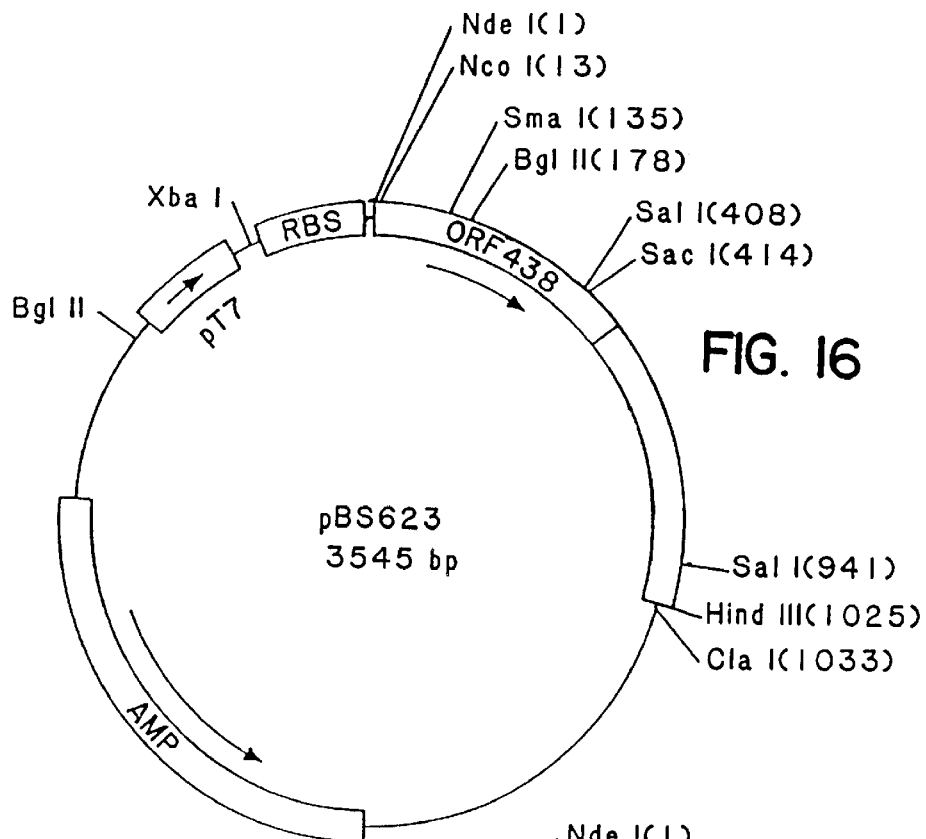
FIG. 16. Plasmid map of pBS623.

Plasmid pBS620.3 was partially digested with SalI to remove region 954-1221 in order to destroy tyrosinase activity. The fragment was isolated and re-ligated to produce pBS623, shown in FIG. 16. An E. *coli* strain containing the mel plasmid pBS623 produced a truncated, inactive tyrosinase which is 69 amino acids shorter than wild-type tyrosinase.

Figure 13A:
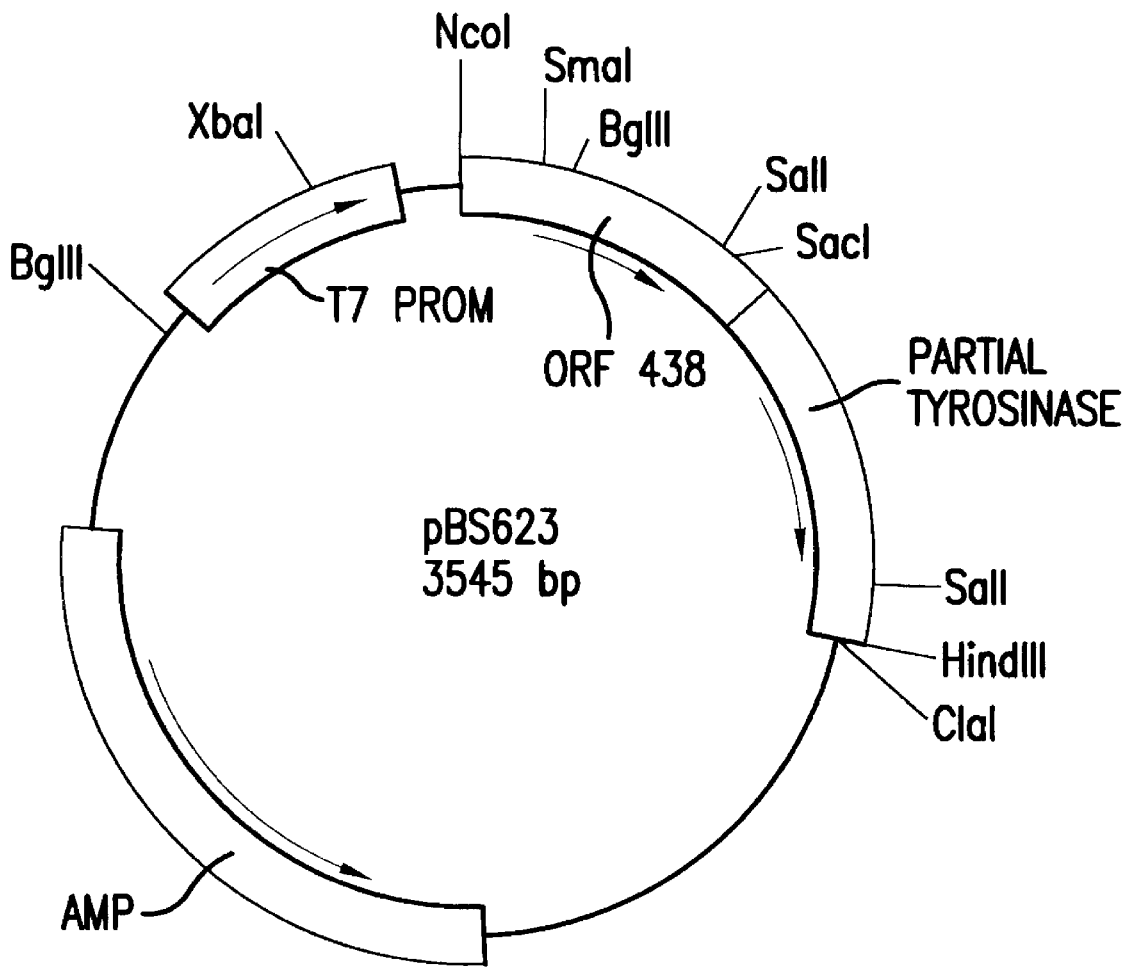
FIG. 13. Shows the construction of pBS634.
Figure 13B:
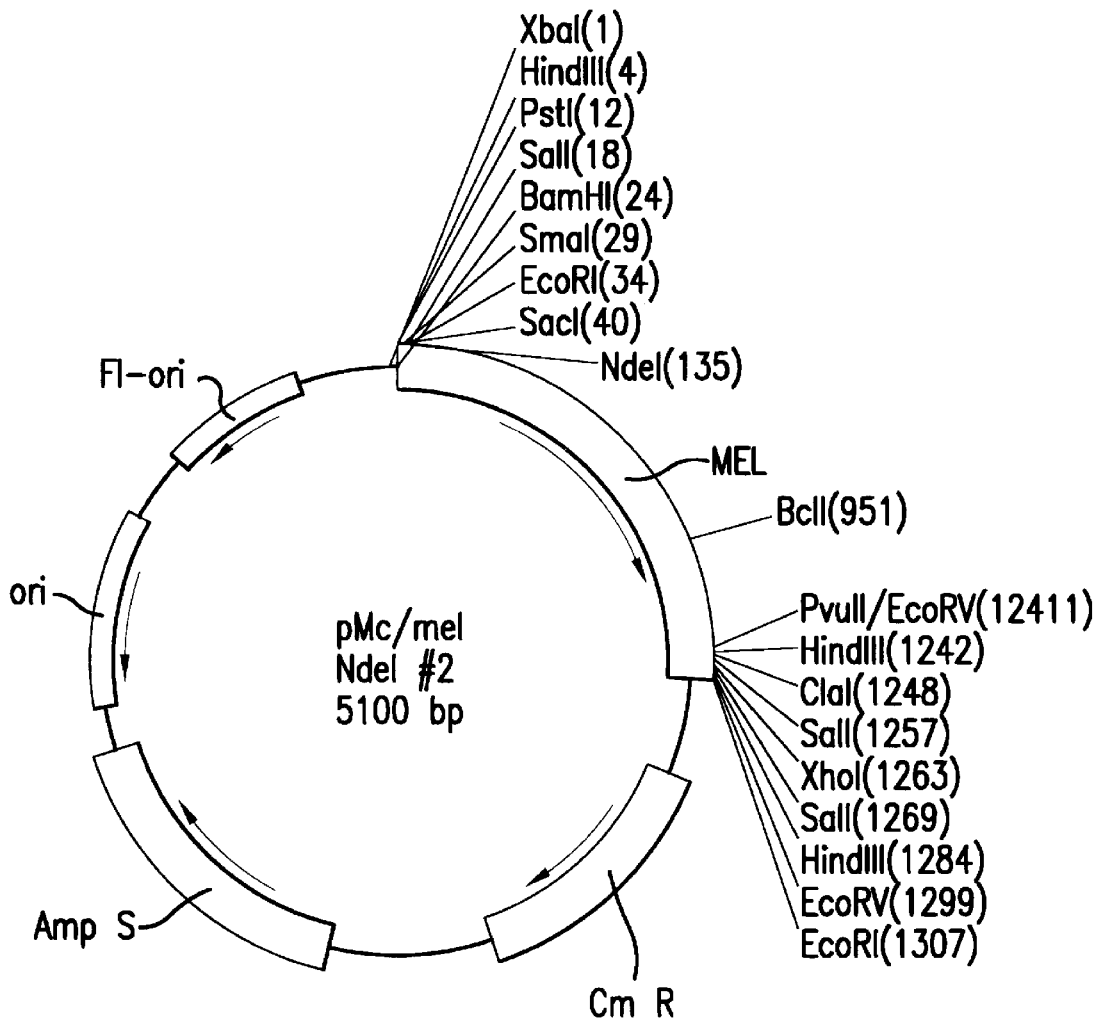
Figure 13C:
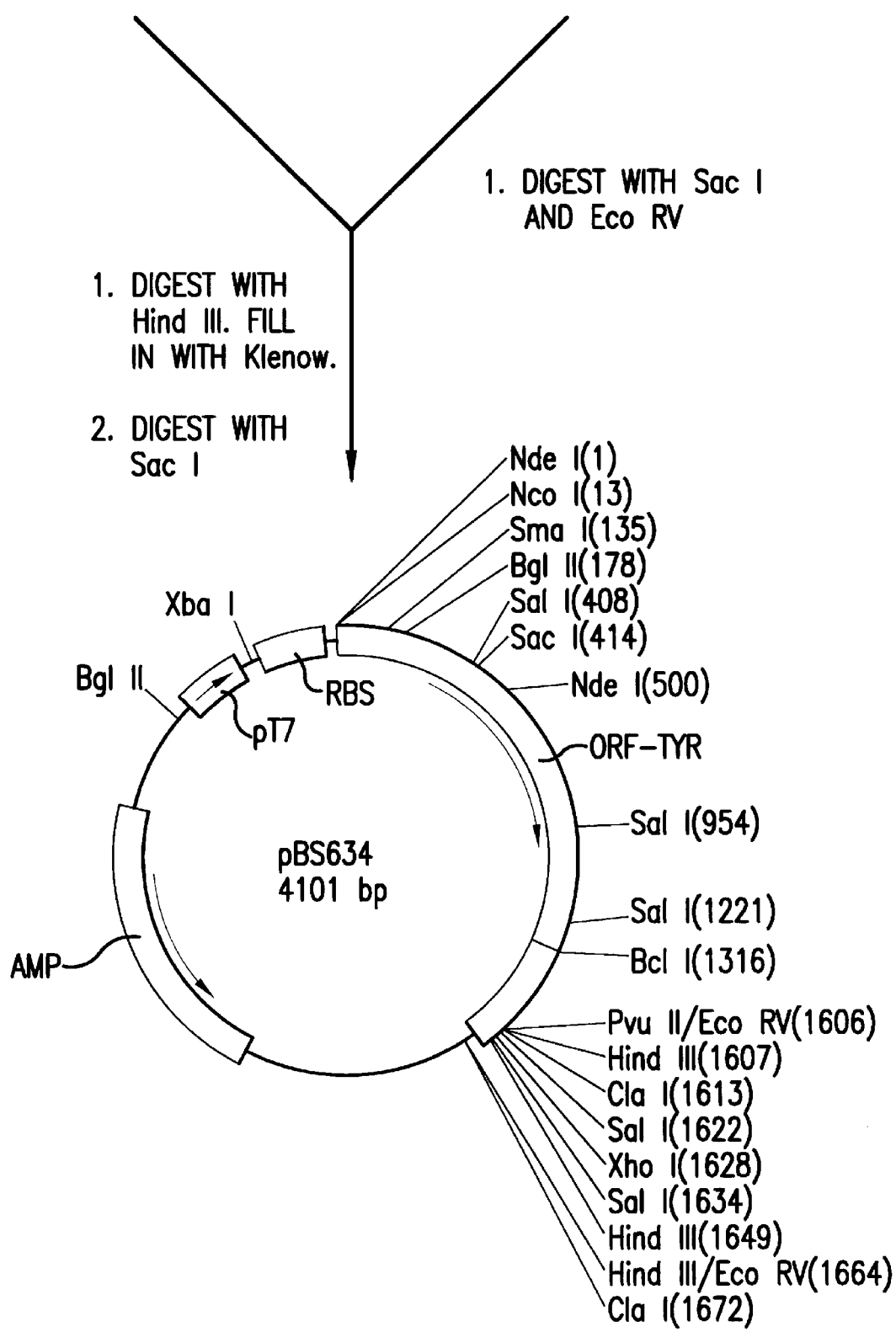
Figure 14:
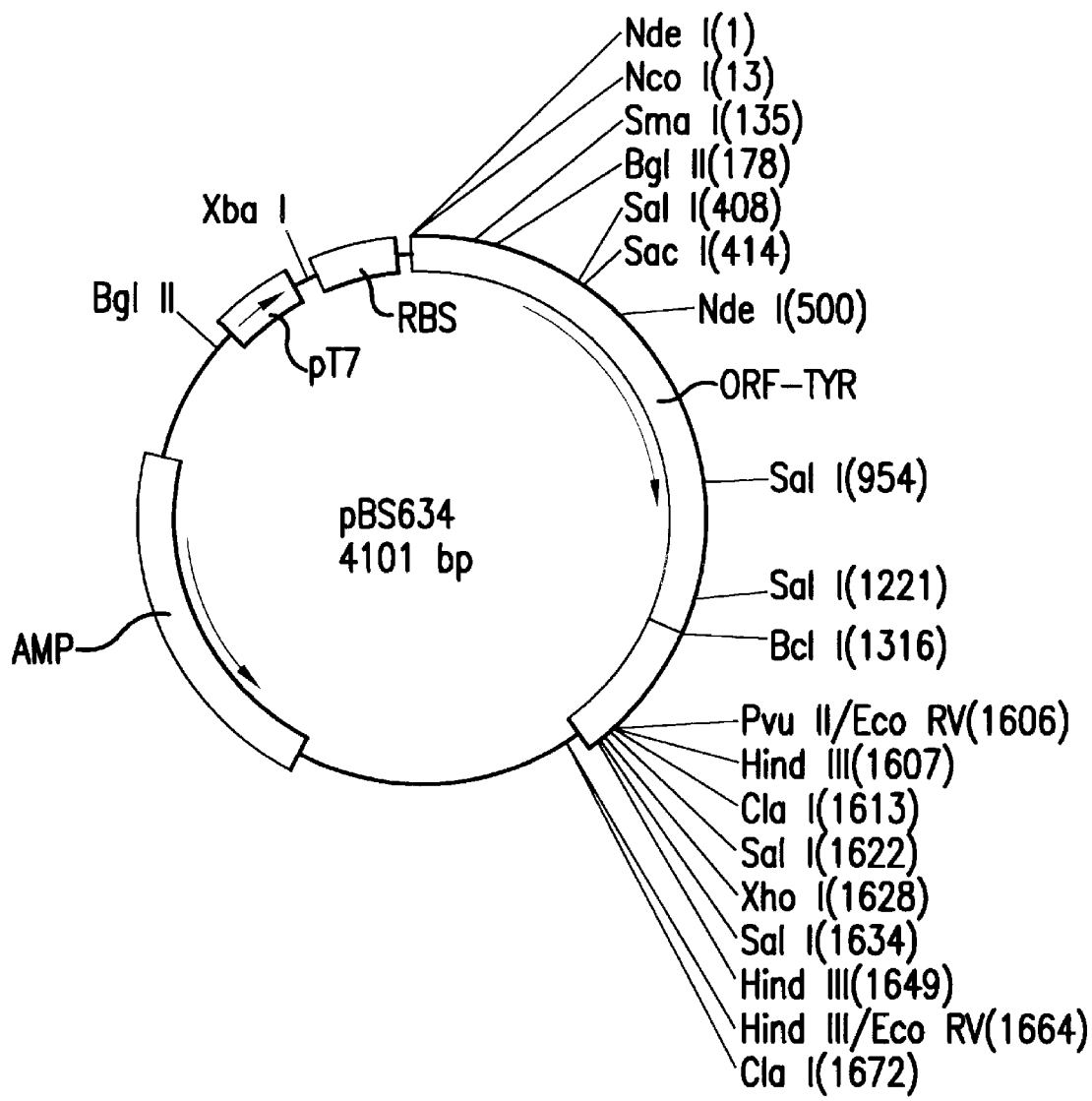
FIG. 14. Plasmid map of pBS634.

Plasmid pBS634 was prepared as shown in FIG. 13. Briefly, the EcoRI fragment from pBS130 containing the mel gene (ORF438/tyrosinase of pIJ702) was cloned into the EcoRI site of pMac5-8 and pMc5-8. An NdeI site was engineered at the start codon of tyrosinase using oligonucleotide-directed mutagenesis according to the protocol of Kramer and Fritz, *Meth.Enzymol.* 154, 350 to produce the plasmid pMc/mel NdeI #2. The SacI/EcoRV fragment of pMc/mel NdeI #2 containing the mel gene with an NdeI site at the start codon of tyrosinase was subcloned into pES623 after pBS623 was digested with HindIII, filled in with the Klenow fragment and digested with SacI to remove the SacI/HindIII fragment. The resulting vector was identified as pBS634 and its map is shown in FIG. 14.

Figure 15:
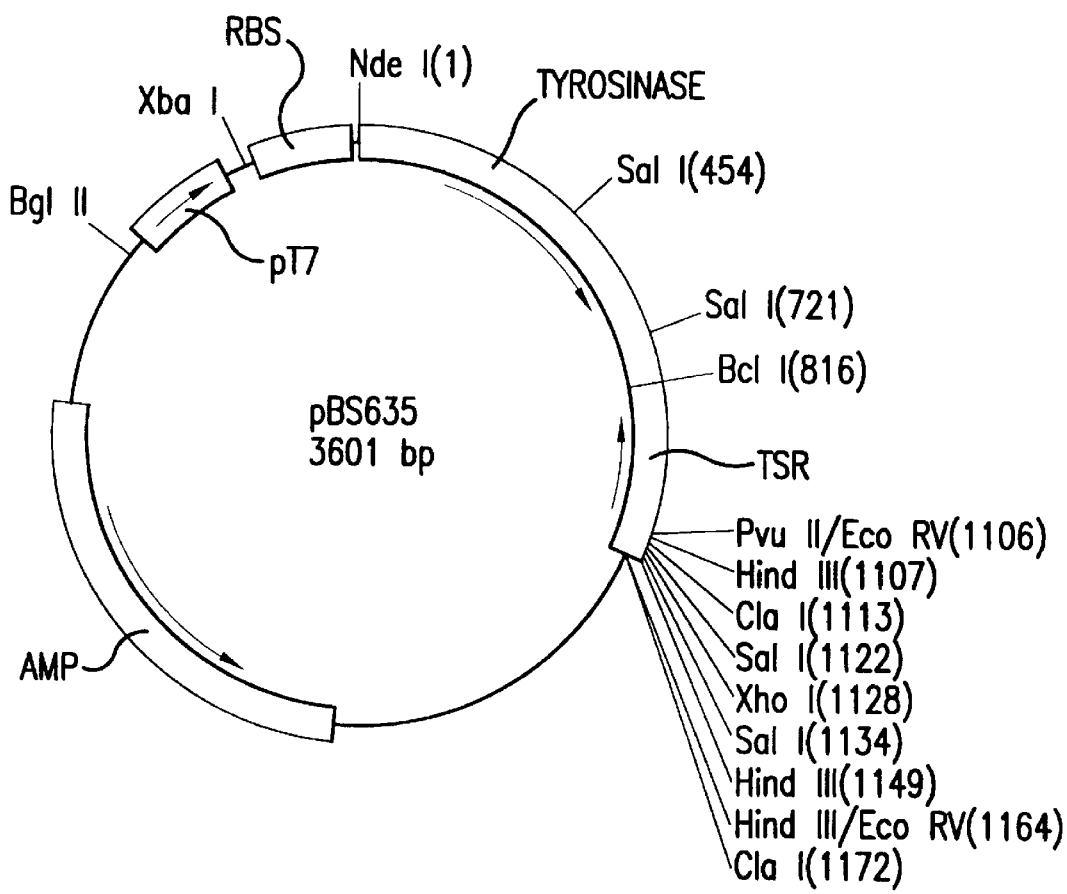
FIG. 15. Plasmid map of pBS635.

The NdeI/BclI fragment from pBS634 containing the ORF-tyrosinase gene was isolated and cloned into pT7-7 to produce pBS635 shown in FIG. 15. The tyrosinase coding sequence is positioned behind the T7 promoter and gene 10 ribosome binding site (RBS) in pBS635. The BglII/BclI fragment from pBS635 containing the newly constructed T7 promoter/RBS/tyrosinase coding sequence was cloned into the BglII site of pBS623 to produce pBS636 shown in FIG. 17. As seen in FIG. 17, pBS636 has two T7 promoters that independently drive the ORF438 and tyrosinase genes. Each of these genes is also constructed to utilize a T7 ribosome binding site instead of their native ribosome binding sites.

EXAMPLE 15

E. *coli* K38 (pGP1-2)/pBS620.3 or pBS636 was grown as described in Example 9 and the medium assayed for melanin production as described in Example 9. At least a four-fold increase in melanin production was seen with pB636, as compared with pBS620.3.

While the invention has been disclosed by reference to the details of preferred embodiments, the disclosure is intended in an illustrative rather than in a limiting sense, as it is contemplated that modifications will readily occur to those skilled in the art, within the spirit of the invention and the scope of the appended claims.

What is claimed is:

1. A method for over-producing melanins, comprising:
    (a) growing a melanin-producing Streptomyces microorganism in a medium comprising;
        (i) casein hydrolysate or casein peptone as a nitrogen source;

(ii) CuSO$_4$-5H$_2$O;
(iii) 20–90% dissolved oxygen; and
(iv) between 1.2 and 1.6 g/l of L-tyrosine, or an amount sufficient to saturate the solution during fermentation, wherein said growth medium does not comprise a carbohydrate as an energy source; and (b) extracting said melanins from the growth medium.

2. The method of claim 1 wherein the melanins are extracted from the growth medium by acid precipitation or by reverse osmosis.

3. The method of claim 1 wherein the Streptomyces microorganism is transformed by a vector which contains one or more DNA sequences coding for an enzyme encoded by a tyrosinase gene or by the Streptomyces ORF438 gene.

4. A method of over-producing melanins, comprising;
   (a) selecting a DNA sequence coding for an enzyme encoded by a tyrosinase gene or by the Streptomyces ORF438 gene;
   (b) inserting at least one copy of said DNA sequence into a vector 3' to a Streptomyces promoter;
   (c) transforming a Streptomyces microorganism with said vector to produce a transformed Streptomyces microorganism;
   (d) growing said transformed Streptomyces microorganism in a growth medium comprising:
      (i) casein hydrolysate or casein peptone as a nitrogen source;
      (ii) CUSO$_4$-5H$_2$O;
      (iii) 20–90% dissolved oxygen; and
      (iv) between 1.2 and 1.6 g/l of L-tyrosine, or an amount sufficient to saturate the solution during fermentation, wherein said growth medium does not comprise a carbohydrate as an energy source; and
   (b) extracting said melanins from the growth medium.

5. The method of claim 4, wherein said DNA sequence codes for tyrosinase and is obtained from a fungus, a bacterium, a human, an animal or a plant.

6. The method of claim 4, wherein the vector is a plasmid or bacteriophage derived from SLP1, pIJH101, ØCS1, pIJ702, M13 or pUC.

7. A method for over-producing melanins, comprising:
   (a) growing a Streptomyces bacterium containing a gene coding for an enzyme encoded by a tyrosinase gene or by the Streptomyces ORF438 gene in a growth medium comprising:
      (i) casein hydrolysate or casein peptone as a nitrogen source;
      (ii) CuSO$_4$-5H$_2$O;
      (iii) 20–90% dissolved oxygen; and
      (iv) between 1.2 and 1.6 g/l of L-tyrosine, or an amount sufficient to saturate the solution during fermentation, wherein said growth medium does not comprise a carbohydrate as an energy source; and
   (b) extracting said melanins from the growth medium.

8. The method of claim 7 wherein said Streptomyces is *S. lividans* TK64 (ATCC 35287) containing the vector pIJ702.

9. A method of over-producing melanins, comprising:
   (a) inoculating a Streptomyces microorganism in a growth medium comprising:
      (i) casein hydrolysate or casein peptone as a nitrogen source;
      (ii) CuSO$_4$-5H$_2$O;
      (iii) 20–90% dissolved oxygen; and
      (iv) between 1.2 and 1.6 g/l of L-tyrosine, or an amount sufficient to saturate the solution during fermentation, wherein said growth medium does not comprise a carbohydrate as an energy source;
   (b) growing said Streptomyces microorganism until the concentration of extracellular melanins in the medium is at least 0.2 grams dry weight per liter; and
   (c) extracting said extracellular melanins from the growth medium.

10. The method of claim 9 wherein said microorganism is *S. lividans* TK64 (ATCC 35287) containing the vector pIJ702.

11. A method of over-producing melanins, comprising:
   (a) selecting a DNA sequence coding for an enzyme encoded by a tyrosinase gene or by the Streptomyces ORF438 gene;
   (b) inserting at least one copy of said DNA sequence into a vector 3' to a Streptomyces promoter;
   (c) transforming a Streptomyces bacterium with said vector to produce a transformed Streptomyces microorganism;
   (d) growing said transformed Streptomyces microorganism in a growth medium comprising:
      (i) casein hydrolysate or casein peptone as a nitrogen source;
      (ii) CuSO$_4$-5H$_2$O;
      (iii) 20–90% dissolved oxygen; and
      (iv) between 1.2 and 1.6 g/l of L-tyrosine, or an amount sufficient to saturate the solution during fermentation, wherein said growth medium does not comprise a carbohydrate as an energy source;
   (b) growing said transformed Streptomyces microorganism until the concentration of extracellular melanins in the medium is at least 0.2 grams dry weight per liter; and
   (c) extracting said extracellular melanins from the growth medium.

12. A method of overproducing melanins, comprising:
   (a) growing a Streptomyces bacterium containing a gene coding for an enzyme encoded by a tyrosinase gene or by the Streptomyces ORF438 gene in a growth medium comprising:
      (i) casein hydrolysate or casein peptone as a nitrogen source;
      (ii) CuSO$_4$-5H$_2$O;
      (iii) 20–90% dissolved oxygen; and
      (iv) between 1.2 and 1.6 g/l of L-tyrosine, or an amount sufficient to saturate the solution during fermentation, wherein said growth medium does not comprise a carbohydrate as an energy source;
   (b) growing said transformed Streptomyces microorganism until the concentration of extracellular melanins in the medium is at least 0.2 grams dry weight per liter; and
   (c) extracting said extracellular melanins from the growth medium.

* * * * *